United States Patent
Satoh et al.

(10) Patent No.: US 8,128,404 B2
(45) Date of Patent: Mar. 6, 2012

(54) ARTIFICIAL TEETH EASILY ENABLING BILATERAL BALANCED OCCLUSION

(75) Inventors: Hirokazu Satoh, Kyoto (JP); Kunihiro Fujii, Kyoto (JP); Noriyuki Negoro, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 224 days.

(21) Appl. No.: 12/680,892

(22) PCT Filed: Oct. 1, 2007

(86) PCT No.: PCT/JP2007/069195
§ 371 (c)(1),
(2), (4) Date: Mar. 20, 2010

(87) PCT Pub. No.: WO2009/044443
PCT Pub. Date: Apr. 9, 2009

(65) Prior Publication Data
US 2010/0266988 A1    Oct. 21, 2010

(51) Int. Cl.
*A61C 13/08* (2006.01)
(52) U.S. Cl. ......................................... 433/197; 433/167
(58) Field of Classification Search .................. 433/167, 433/171, 196–198, 202.1
See application file for complete search history.

(56) References Cited

U.S. PATENT DOCUMENTS

| | | | |
|---|---|---|---|
| 943,113 A | 12/1909 | Greenfield | |
| 2,006,717 A | 7/1935 | Phillips | |
| 2,072,127 A * | 3/1937 | Pilkington et al. | 433/197 |
| 2,104,459 A * | 1/1938 | Gysi | 433/197 |
| D114,512 S | 4/1939 | Settell | |
| 2,416,983 A * | 3/1947 | Dickson | 433/197 |
| 2,570,562 A * | 10/1951 | Kinsley | 433/197 |
| 2,585,857 A | 2/1952 | Schwartz | |
| 2,874,832 A | 2/1959 | Gordon | |
| 3,105,300 A * | 10/1963 | Beresin | 433/197 |
| 3,247,844 A | 4/1966 | Berghash | |
| 3,423,831 A | 1/1969 | Semmelman | |
| 3,638,309 A * | 2/1972 | Frush | 433/197 |
| 3,947,963 A * | 4/1976 | Haker | 433/197 |

(Continued)

FOREIGN PATENT DOCUMENTS

DE    4432176 A1    3/1996

(Continued)

OTHER PUBLICATIONS

Toshio Hayashi et al., Complete Denture Prosthetics, Ishiyaku Pub. Inc., Apr. 10, 1982, pp. 309-311.

(Continued)

*Primary Examiner* — John J Wilson
(74) *Attorney, Agent, or Firm* — Capitol City TechLaw

(57) ABSTRACT

It is intended to provide artificial teeth designed to easily enable bilateral balanced occlusion with less grinding adjustment. According to the present invention, angles formed by occlusal facets of the artificial teeth with an occlusal plane are suitably set. An artificial tooth for maxillary central incisor, for example, has a protrusive facet and a retrusive facet on an incisal edge thereof. Of angles formed by the protrusive facet with the occlusal plane, the angle in cross section along a sagittal plane is 22.0° to 25.5°, and the angle in cross section along a coronal plane is 1.5° to 6.5°. Of angles formed by the retrusive facet with the occlusal plane, the angle in cross section along the sagittal plane is 20.5° to 23.0°, and the angle in cross section along the coronal plane is 1.5° to 6.5°.

9 Claims, 19 Drawing Sheets

U.S. PATENT DOCUMENTS

| | | | |
|---|---|---|---|
| 4,194,288 A * | 3/1980 | Hass | 433/197 |
| 4,208,794 A * | 6/1980 | Gerber | 433/197 |
| D272,465 S | 1/1984 | Wolf | |
| 4,445,863 A | 5/1984 | Lang et al. | |
| 4,481,162 A | 11/1984 | Huffman | |
| 4,523,912 A | 6/1985 | Breustedt et al. | |
| 4,626,215 A * | 12/1986 | Clarke | 433/198 |
| 4,872,840 A | 10/1989 | Bori | |
| 4,911,641 A | 3/1990 | Detsch | |
| 4,969,817 A | 11/1990 | Hiranuma et al. | |
| 4,997,373 A | 3/1991 | Tanaka et al. | |
| 5,051,091 A | 9/1991 | Rosenfeld | |
| 5,232,370 A | 8/1993 | Hoye | |
| 5,234,339 A | 8/1993 | Grigereit | |
| 5,326,262 A * | 7/1994 | Jorgenson | 433/197 |
| 5,733,125 A * | 3/1998 | Foser | 433/197 |
| 5,788,489 A | 8/1998 | Huffman | |
| 5,788,490 A | 8/1998 | Huffman | |
| 5,906,489 A | 5/1999 | Khazzam et al. | |
| 5,951,289 A | 9/1999 | Kura et al. | |
| 6,394,810 B1 | 5/2002 | Choi | |
| 6,431,868 B2 | 8/2002 | Story | |
| 6,488,503 B1 | 12/2002 | Lichkus et al. | |
| 6,508,651 B1 * | 1/2003 | Nakamura et al. | 433/197 |
| 6,533,581 B1 | 3/2003 | Moenckmeyer | |
| 6,790,035 B2 | 9/2004 | Tricca et al. | |
| 7,059,850 B1 | 6/2006 | Phan et al. | |
| 7,108,511 B1 | 9/2006 | Shatkin | |
| 7,201,576 B2 | 4/2007 | Tricca et al. | |
| 7,699,610 B2 | 4/2010 | Childress | |
| 2003/0031981 A1 | 2/2003 | Holt | |
| 2005/0095559 A1 | 5/2005 | Monkmeyer | |
| 2006/0263749 A1 | 11/2006 | Koide | |
| 2010/0119992 A1 | 5/2010 | Satoh et al. | |

FOREIGN PATENT DOCUMENTS

| | | |
|---|---|---|
| DE | 19508762 C1 | 5/1996 |
| GB | 2433444 A | 6/2007 |
| JP | D777064 | 12/1989 |
| JP | D7770641 | 4/1990 |
| JP | 08112294 | 5/1996 |
| JP | 10504985 | 5/1998 |
| JP | 11290347 | 10/1999 |
| JP | 2002177301 A | 6/2002 |
| JP | 2002523134 A | 7/2002 |
| JP | 2003102752 A | 4/2003 |
| JP | D1197057 | 2/2004 |
| JP | D1197058 | 2/2004 |
| JP | D1197530 | 2/2004 |
| JP | D1202523 | 4/2004 |
| JP | D1202524 | 4/2004 |
| JP | D1203086 | 4/2004 |
| JP | D1203087 | 4/2004 |
| JP | D1203088 | 4/2004 |
| JP | D1203089 | 4/2004 |
| JP | D1203090 | 4/2004 |
| JP | D1203091 | 4/2004 |
| JP | 2005525841 A | 9/2005 |
| JP | 3747251 B2 | 2/2006 |
| WO | 9607365 | 3/1996 |

OTHER PUBLICATIONS

Hiromichi Tsuru et al., Complete Denture Technique, Third Edition, Ishiyaku Pub. Inc., Oct. 30, 1993, pp. 141-143.

S.S. White's Dental Catalog, 1876, pp. 22-23, Figs. 4 through 7, illustrations of artificial teeth from the side profile.

The S.S. White Dental Mfg. Co. Catalog, 1890, p. 84, Figs. 2 and 3 showing an artificial tooth with dimple and mounting pin.

The S.S. White Dental Mfg. Co. Crown and Bridge Works Catalog, 1899, p. 108, Hollingsworth's crown and bridge work system Set Nos. 1 and 2.

S.S. White Dental Mfg. Co., Operative Instruments and Accessories. Catalog "F", 1907, p. 76, Fig. 8 showing artificial teeth with dimple area for mounting pin.

Oxford University of Natural History/the Learning Zone. Upper and Lower teeth. Copyright 2006.

Yeti Dental Flier, 1994/95, p. 30 showing images of artificial molars at the bottom of the page.

Shofu Inc., Veracia SA Anterior and Posterior Q-Pack brochure, published Mar. 2011.

* cited by examiner (a)

(b)

(a)

(b)

(a)

(b)

(a)

(b)

(a)

(b)

(a)

(b)

(a)

(b)

ARTIFICIAL TEETH EASILY ENABLING BILATERAL BALANCED OCCLUSION

TECHNICAL FIELD

The present invention relates to preliminarily polymerized and cured artificial teeth to be used in the production of a denture having a base plate.

BACKGROUND TECHNOLOGY

An artificial tooth is a dental material used by an odontologist or a dental technician in the production of a denture having a base plate. Among the artificial teeth ranging in different sizes and shapes, a tooth suitable for a patient's missing tooth and a therapeutic approach is chosen and used.

To produce the artificial tooth, a patient's intraoral counterdie is formed from an impression material and plaster is poured into the counterdie and then hardened to make a model. The model is then mounted on a device for replicating gnathic motion, called an articulator, to perform a work on the model.

Examples of the articulator are an adjustable articulator in which guide path angles of joint articulations in lateral movements of the denture can be adjustably set, and a mean value articulator in which these angles are set to mean angles of human. In the case where an odontologist determines that any particular angle adjustments are unnecessary, the mean value articulator is used.

In prosthodontic treatment using a complete denture, it is desirable to accomplish an occlusal state, generally called, bilateral balanced occlusion. There are two types of bilateral balanced occlusion, full-balanced occlusion and balanced occlusion. The full-balanced occlusion denotes an occlusal relation where all of teeth simultaneously make contacts in intercuspation and in all of eccentric movements. Clinically, however, the replication is quite difficult due to, for example, errors generated in alignment and grinding adjustment, which leaves the balanced occlusion as a practical option. The balanced occlusion denotes an occlusal relation where several teeth may not make any contact as far as there is gliding motility in two or three teeth on a working side and two or three teeth on a balancing side in the eccentric movements. According to the balanced occlusion, therefore, a denture adapted to mandibular movements, which is different in each patient, can be produced through preliminary grinding adjustment during the production of the denture followed by final adjustments by the odontologist made on the denture intraorally worn by the patient. The working side denotes a side where the row of mandibular teeth shifts to a buccal side relative to the row of maxillary teeth in the lateral movements, and the balancing side denotes a side opposite thereto. When upper and lower jaws are making an occlusal contact and the lower jaw is then moved, for example, the working side is on right, and the balancing side is on left.

In the Patent Document 1, the present Applicant has proposed artificial teeth wherein a relative positional relation between cuspis dentis and fossete is defined.

The manipulation to enable the bilateral balanced occlusion through the grinding adjustment is a very time-consuming and demanding precision work. Therefore, an artificial tooth ground beforehand into a shape in accord with the motility of the mean value articulator was a long-awaited product in the field of odontologistry.

Patent Document 1: JP Laid-Open Patent Publication 2003-102752

DISCLOSURE OF THE INVENTION

Problem to be Solved by the Invention

An object of the present invention is to provide artificial teeth which easily enables an establishment of bilateral balanced occlusion with less grinding adjustment in the production of a complete denture using an articulator wherein an interarch distance is 105 mm, a sagittal condylar guide angle is 25° relative to a horizontal plane, an angle formed by an occlusal triangle with an occlusal plane is 15°, a sagittal incisal guide angle is 10°, and a lateral incisal guide angle is 10°.

Means for Solving the Problem

In the present invention, angles formed by occlusal facets of the following teeth and an occlusal plane are suitably set; an artificial tooth for maxillary central incisor, an artificial tooth for maxillary lateral incisor, an artificial tooth for maxillary canine, an artificial tooth for maxillary first premolar, an artificial tooth for maxillary second premolar, an artificial tooth for maxillary first molar, and an artificial tooth for maxillary second molar. Alos, angles formed by occlusal facets of the following teeth and the occlusal plane are suitably set; an artificial tooth for mandibular central incisor, an artificial tooth for maxillary lateral incisor, an artificial tooth for mandibular canine, an artificial tooth for mandibular first premolar, an artificial tooth for mandibular second premolar, an artificial tooth for mandibular first molar, and an artificial tooth for mandibular second molar.

In the present invention, a contact positional relation between the respective occlusal facets of the maxillary artificial teeth and the mandibular artificial teeth in intercuspation, and a gliding relation between a working side and a balancing side in lateral eccentric movements and between the respective occlusal facets in protrusive movements are suitably set.

Effect of the Invention

When the artificial teeth according to the present invention are used in the production of a denture, it becomes easy to obtain such eccentric movements that there are homogeneous contact and glide between incisal edges of anterior teeth and occlusal facets of posterior teeth of maxillary and mandibular artificial teeth at angles in accord with guide paths of a mean value articulator, resulting in the reduction of an adjustment work. Accordingly, the production of a denture having reliable occlusion can be expedited, which helps to alleviate the burden of intricate work on an odontologist or a dental technician.

DESCRIPTION OF THE REFERENCE SYMBOLSP

Figure 1:
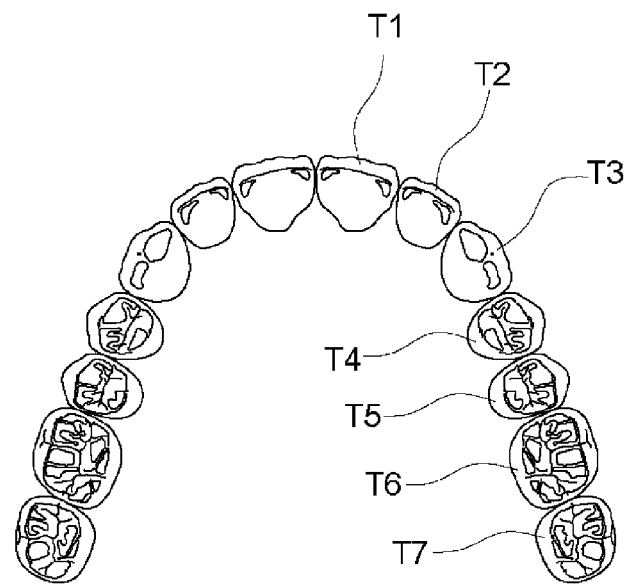
FIG. 1 is a view of occlusal surfaces illustrating the alignment of maxillary and mandibular artificial teeth.
Figure 1:
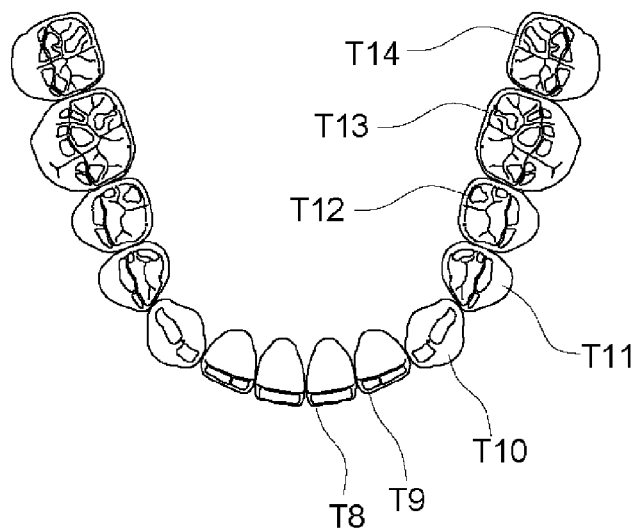

| | |
|---|---|
| T1 | artificial tooth for maxillary central incisor |
| i1 | incisal edge |
| f1 | protrusive facet |
| f2 | retrusive facet |
| T2 | artificial tooth for maxillary lateral incisor |
| i2 | icisal edge |
| f3 | protrusive facet |
| f4 | retrusive facet |
| T3 | artificial tooth for maxillary canine |
| i3 | incisal edge |
| f5 | protrusive facet |
| f6 | retrusive facet |
| T4 | artificial tooth for maxillary first premolar |
| c1 | buccal cusp apex |
| f7 | protrusive facet |
| f8 | retrusive facet |
| c2 | lingual cusp apex |
| f9 | balancing facet |
| T5 | artificial tooth for maxillary second premolar |
| c3 | buccal cusp apex |
| f10 | protrusive facet |
| f11 | retrusive facet |
| c4 | lingual cusp apex |
| f12 | balancing facet |
| T6 | artificial tooth for maxillary first molar |
| c5 | mesiobuccal cusp apex |
| f13 | protrusive facet |
| f14 | retrusive facet |
| c6 | distobuccal cusp apex |
| f15 | protrusive facet |
| f16 | retrusive facet |
| c7 | mesiobuccal cusp apex |
| f17 | balancing facet |
| f18 | protrusive facet |
| c8 | distolingual cusp apex |
| f19 | retrusive facet |
| f20 | balancing facet |
| T7 | artificial tooth for maxillary second molar |
| c9 | mesiobuccal cusp apex |
| f21 | protrusive facet |
| f22 | retrusive facet |
| c10 | distobuccal cusp apex |
| f23 | retrusive facet |
| c11 | mesiolingual cusp apex |
| f24 | balancing facet |
| f25 | protrusive facet |
| T8 | artificial tooth for mandibular central incisor |
| i4 | incisal edge |
| f26 | protrusive facet |
| T9 | artificial tooth for mandibular lateral incisor |
| i5 | incisal edge |
| f27 | protrusive facet |
| f28 | retrusive facet |
| T10 | artificial tooth for mandibular canine |
| i6 | incisal edge |
| f29 | protrusive facet |
| f30 | retrusive facet |
| T11 | artificial tooth for mandibular first premolar |
| c12 | buccal cusp apex |
| f31 | protrusive facet |
| f32 | retrusive facet |
| s1 | distal fossete |
| f33 | balancing facet |
| f34 | protrusive facet |
| T12 | artificial tooth for mandibular second premolar |
| c13 | buccal cusp apex |
| f35 | protrusive facet |
| f36 | retrusive facet |
| s2 | distal fossete |
| f37 | balancing facet |
| f38 | protrusive facet |
| T13 | artificial tooth for mandibular first molar |
| c14 | mesiobuccal cusp apex |
| f39 | protrusive facet |
| f40 | retrusive facet |
| f41 | balancing facet |
| c15 | distobuccal cusp apex |
| f42 | protrusive facet |
| f43 | retrusive facet |
| f44 | balancing facet |
| c16 | distal cusp apex |
| f45 | protrusive facet |
| f46 | balancing facet |
| s3 | central fossa |
| f47 | protrusive facet |
| T14 | artificial tooth for mandibular second molar |
| c17 | mesiobuccal cusp apex |
| f48 | protrusive facet |
| f49 | retrusive facet |
| f50 | balancing facet |
| c18 | distobuccal cusp apex |
| f51 | protrusive facet |

-continued

| | |
|---|---|
| f52 | retrusive facet |
| f53 | balancing facet |
| s4 | central fossa |
| f54 | protrusive facet |
| P1 | occlusal plane |
| P2 | sagittal plane |
| P3 | coronal plane |

BEST MODE FOR CARRYING OUT THE INVENTION (Description of Reference Planes)

Below are described names of reference planes used in the description of a preferred embodiment of the present invention.

An occlusal plane anatomically denotes an imaginary plane including an incisal point in the row of maxillary or mandibular teeth and cusp apexes of extremitas posterior teeth on left and right. When the present invention is actually carried out, an occlusal plane board of an articulator represents the occlusal plane.

A sagittal plane denotes a plane orthogonal to an intercondylar axis, dividing a human body into left and right portions.

A coronal plane is a plane orthogonal to the sagittal plane and a horizontal plane.

The horizontal plane denotes a plane in parallel with a ground surface.

(Requirements for Articulator)

In an articulator in which artificial teeth according to the present invention are used, an intercondylar distance (distance between rotational centers of left and right caput mandibulae) is 105 mm, a sigittal condylar guide angle (mandibular movements path in mandibular protrusive movements projected on the sagittal plane) relative to the horizontal plane is 25.0°, an angle formed by an occlusal triangle (plane including a triangle obtained by connecting the rotational centers of left and right caput mandibulae to an incisal point on the occlusal plane board) with the occlusal plane is 15.0°, a sagittal incisal guide angle (angle formed by a line with the reference horizontal plane, the line obtained by connecting an incisal point when the mandibulae are in intercuspation to an incisal point when upper and lower anterior teeth protrusively move and meet in intercuspation on incisal edges thereof) is 10.0°, and a lateral incisal guide angle (angle formed by a line with the reference horizontal plane, the line obtained by connecting the incisal point when the mandibulae are in intercuspation to an incisal point when upper and lower anterior teeth laterally move and meet in intercuspation on incisal edges thereof) is 10.0°. The occlusal plane board should be in parallel with the horizontal plane. An adjustable articulator adjusted to meet the requirements may be used.

Figure 2:
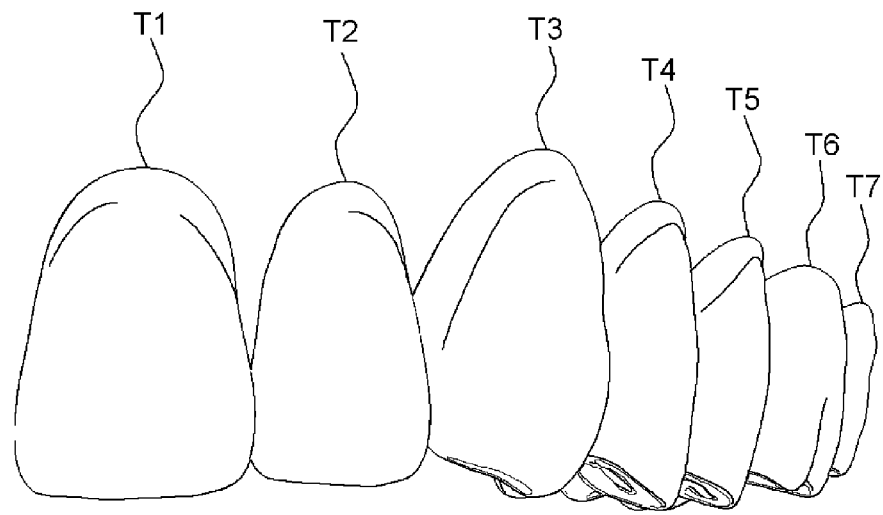
FIG. 2 is a front view of the maxillary and mandibular artificial teeth observed in a direction perpendicular to a coronal plane.
Figure 2:
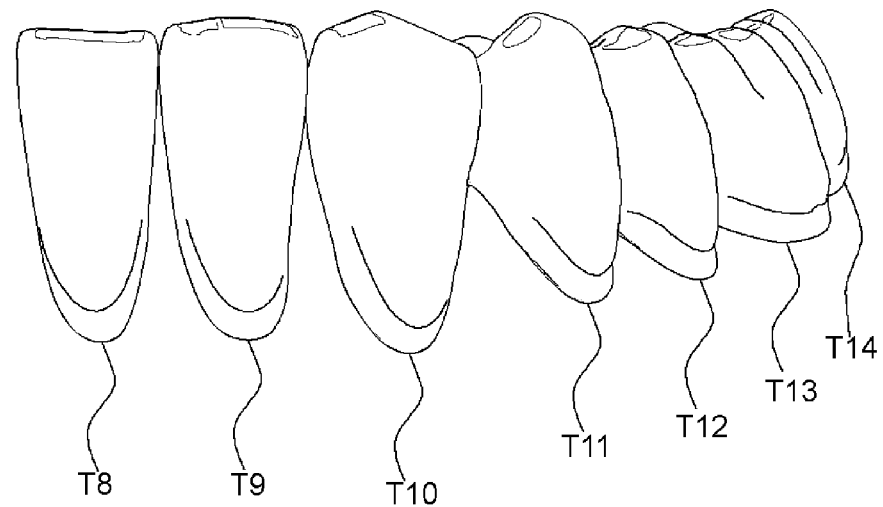
Figure 3:
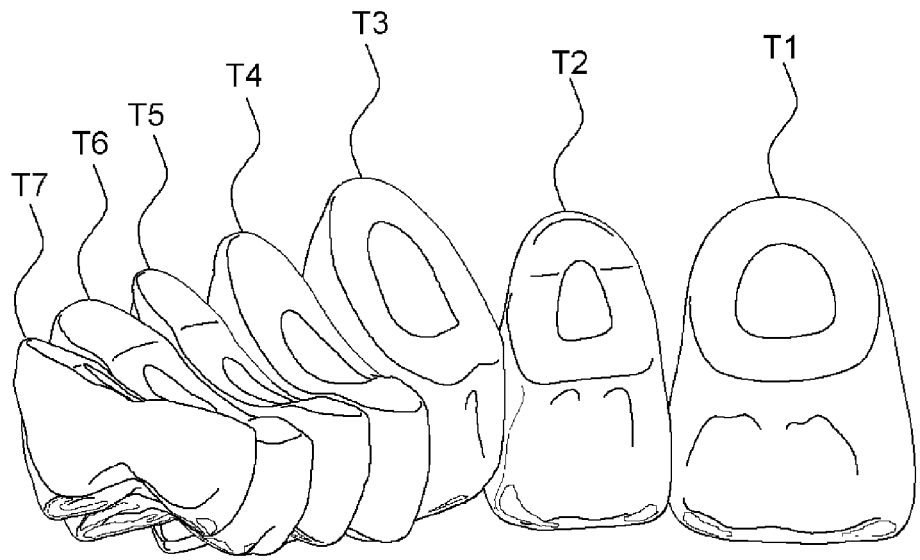
FIG. 3 is a rear view of the maxillary and mandibular artificial teeth observed in the direction perpendicular to the coronal plane.
Figure 3:
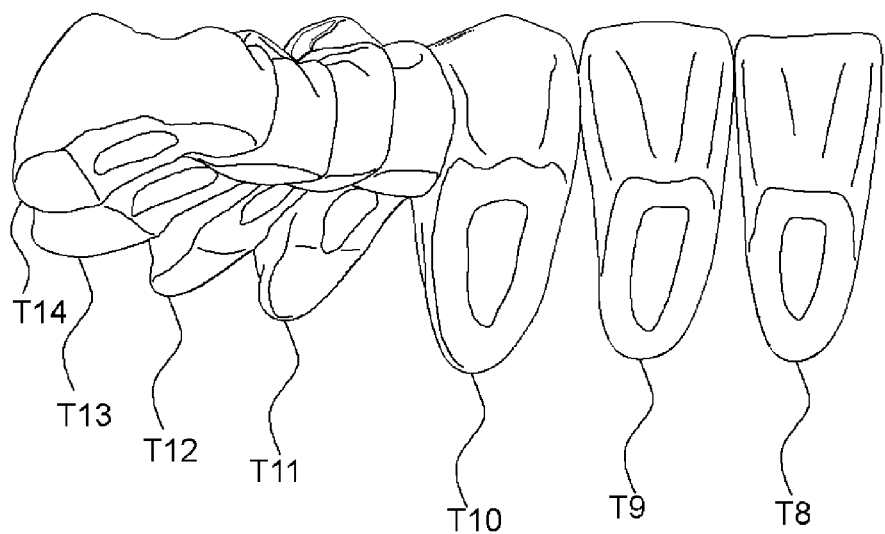
Figure 4:
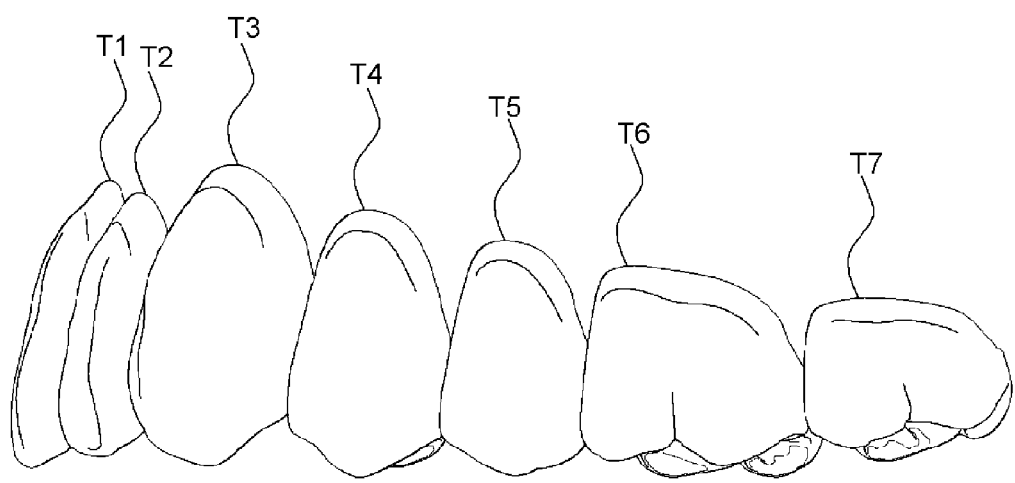
FIG. 4 is a front view of the maxillary and mandibular artificial teeth observed in a direction perpendicular to a sagittal plane.
Figure 4:
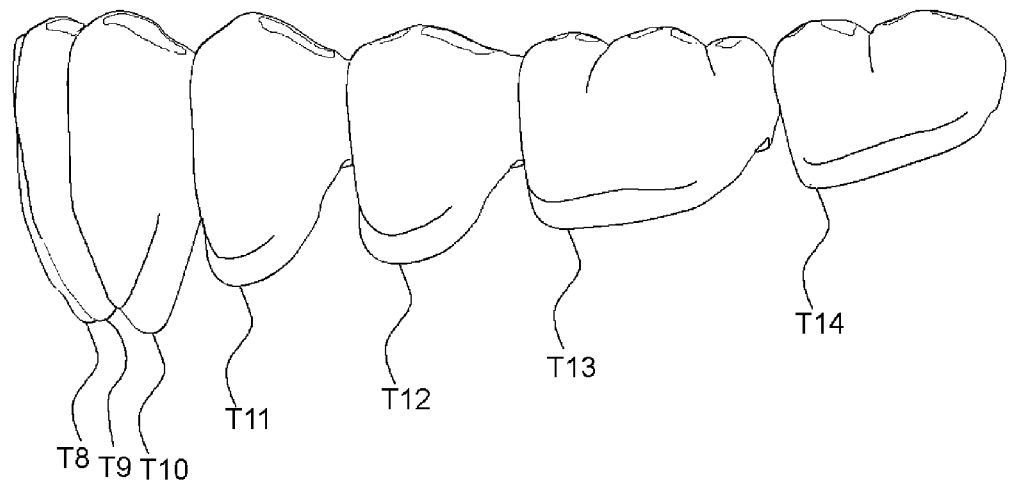
Figure 5:
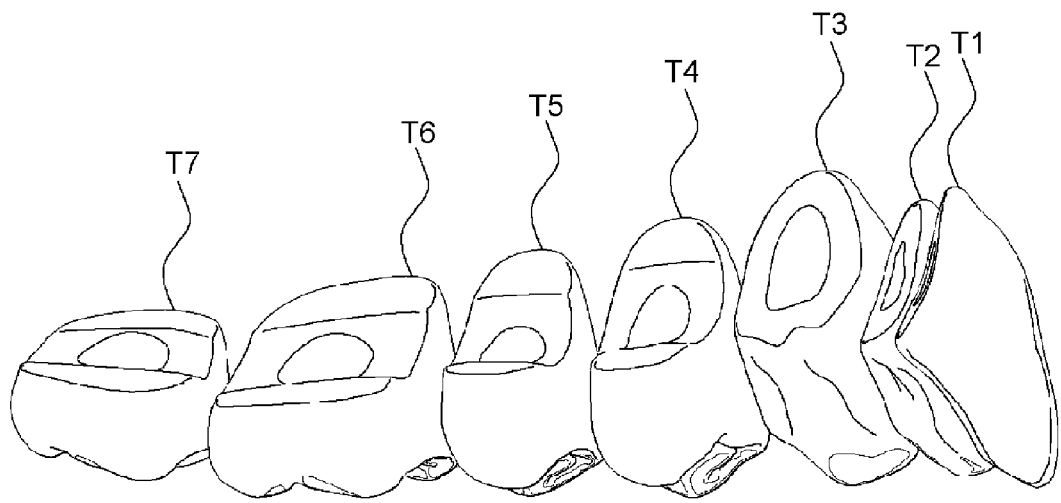
FIG. 5 is a rear view of the maxillary and mandibular artificial teeth observed in the direction perpendicular to the sagittal plane.
Figure 5:
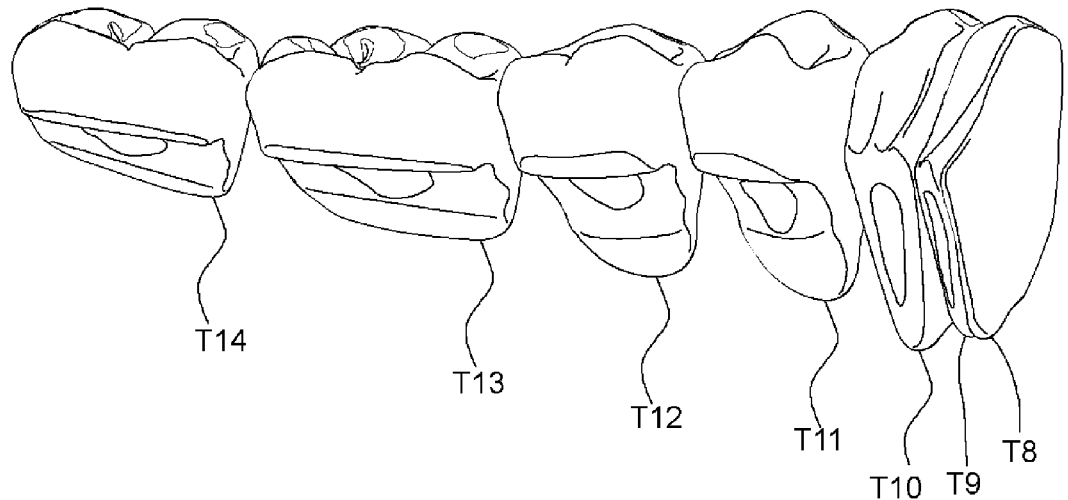
Figure 6:
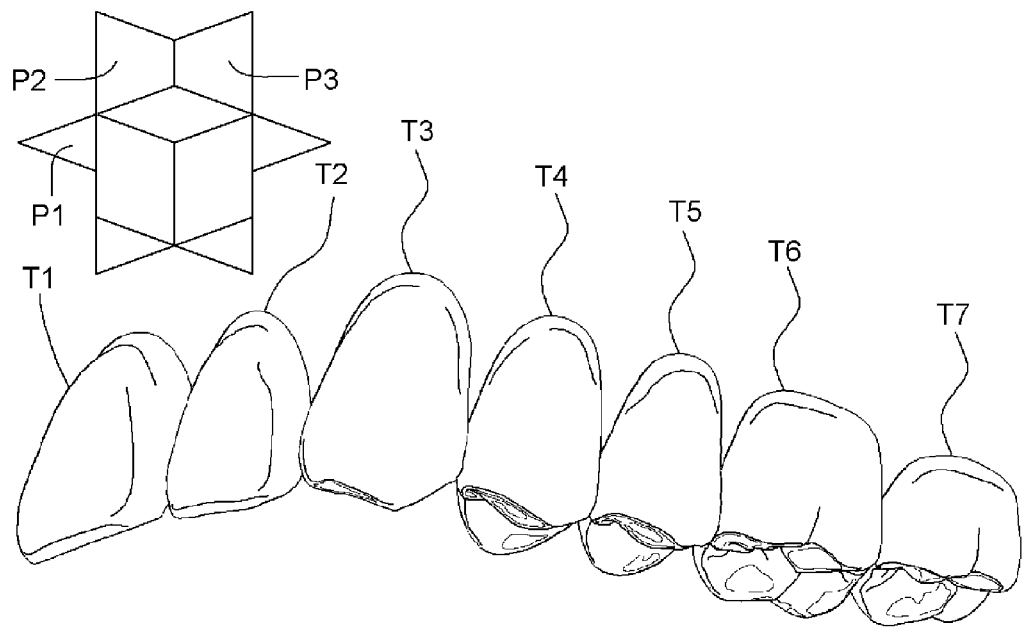
FIG. 6 is a perspective view of the maxillary and mandibular artificial teeth observed from a buccal side.
Figure 6:
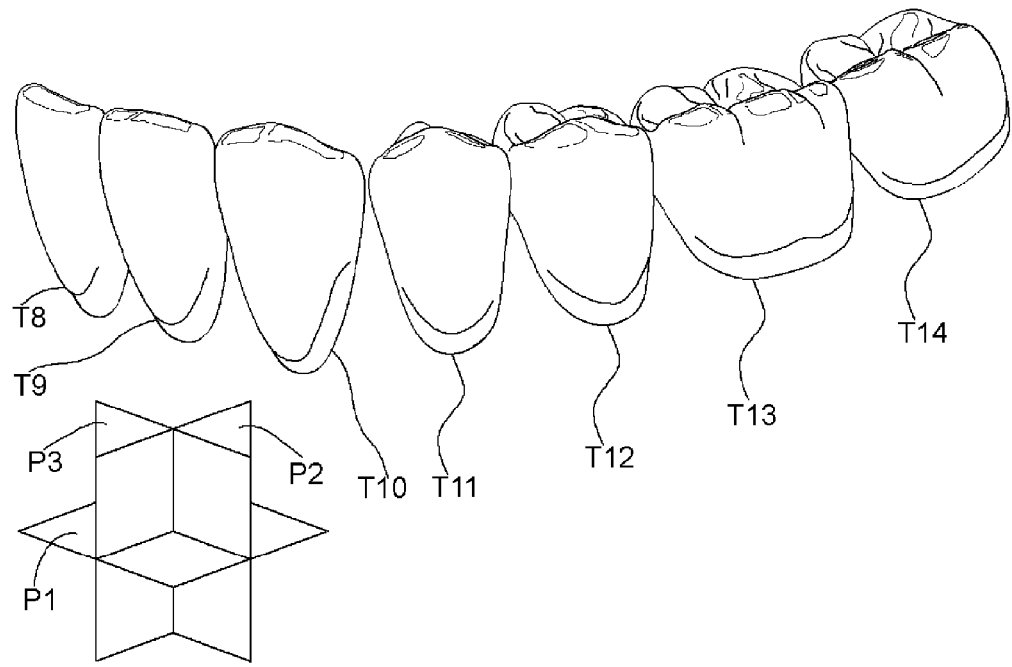
Figure 7:
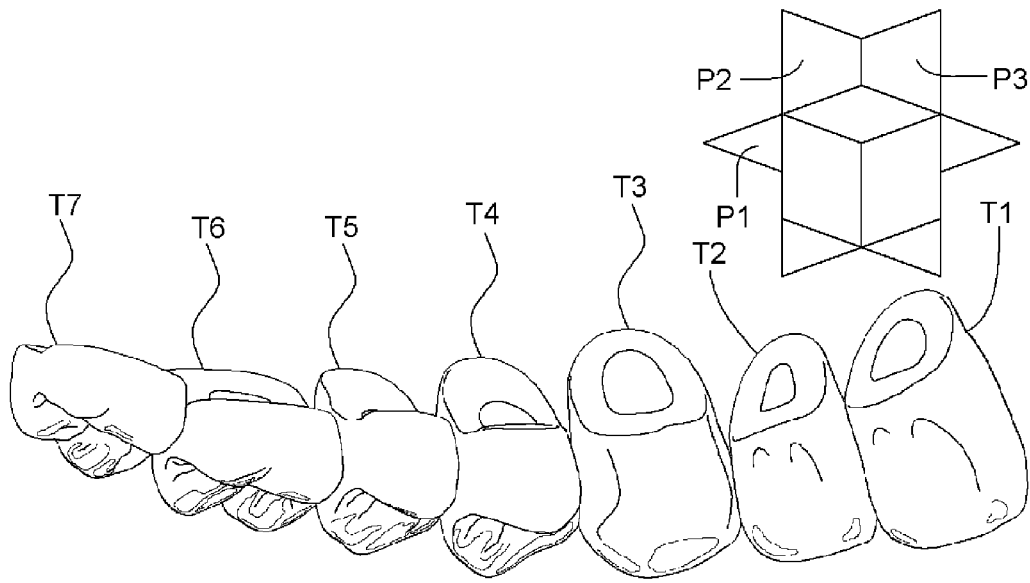
FIG. 7 is a perspective view of the maxillary and mandibular artificial teeth observed from a lingual side.
Figure 7:
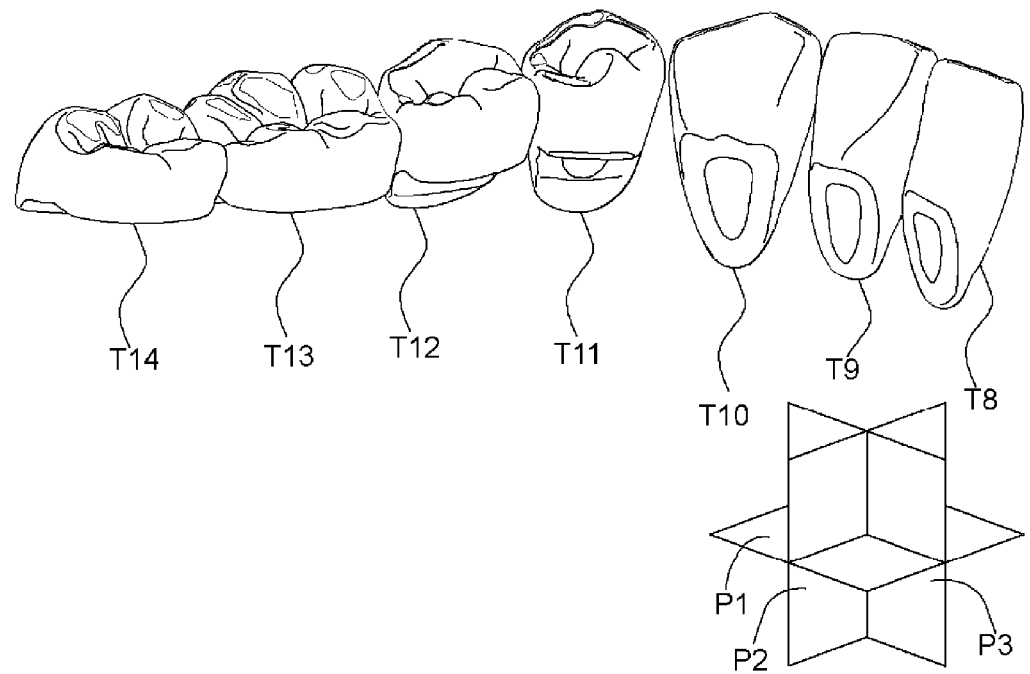

FIG. 1 is a view of occlusal surfaces illustrating the alignment of maxillary and mandibular artificial teeth. FIG. 2 is a front view of the maxillary and mandibular artificial teeth observed in a direction perpendicular to a coronal plane. FIG. 3 is a rear view of the maxillary and mandibular artificial teeth observed in the direction perpendicular to the coronal plane. FIG. 4 is a front view of the maxillary and mandibular artificial teeth observed in a direction perpendicular to a sagittal plane. FIG. 5 is a rear view of the maxillary and mandibular artificial teeth observed in the direction perpendicular to the sagittal plane. FIG. 6 is a perspective view of the maxillary and mandibular artificial teeth observed from a buccal side. FIG. 7 is a perspective view of the maxillary and mandibular artificial teeth observed from a lingual side.

As illustrated in these views, the maxillary artificial teeth include an artificial tooth for maxillary central incisor T1; an artificial tooth for maxillary lateral incisor T2, an artificial tooth for maxillary canine T3, an artificial tooth for maxillary first premolar T4, an artificial tooth for maxillary second premolar T5, an artificial tooth for maxillary first molar T6, and an artificial tooth for maxillary second molar T7. The mandibular artificial teeth similarly include an artificial tooth for mandibular central incisor T8, an artificial tooth for mandibular lateral incisor T9, an artificial tooth for mandibular canine T10, an artificial tooth for mandibular first premolar T11, an artificial tooth for mandibular second premolar T12, an artificial tooth for mandibular first molar T13, and an artificial tooth for mandibular second molar T14.

Figure 8:
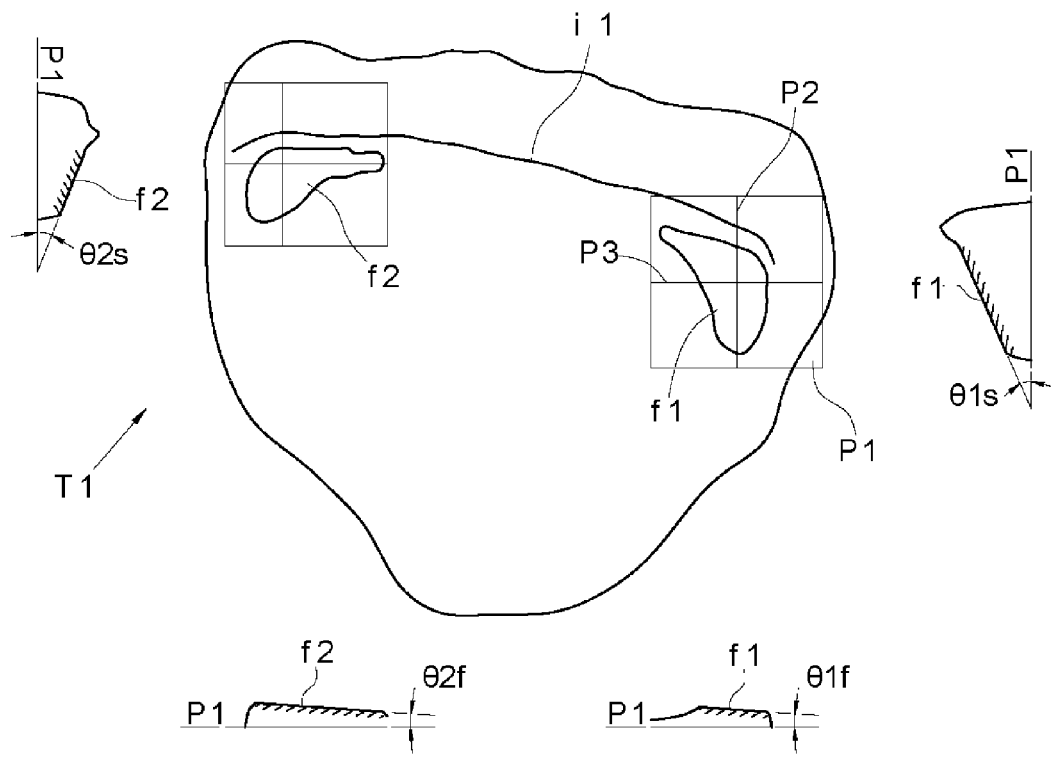
FIG. 8 is a view of an occlusal surface of an artificial tooth for maxillary central incisor.

FIG. 8 illustrates the artificial tooth for maxillary central incisor T1. The artificial tooth for maxillary central incisor T1 has a protrusive facet f1 and a retrusive facet f2 on an incisal edge i1.

Of angles formed by the protrusive facet f1 with the occlusal plane P1, the angle ($\theta$1s) in cross section along the sagittal plane P2 is 22.0° to 25.5°, and preferably 23.5° to 24.5°, and the angle ($\theta$1f) in cross section along the coronal plane P3 is 1.5° to 6.5°, and preferably 3.5° to 4.5°.

Of angles formed by the retrusive facet f2 with the occlusal plane P1, the angle ($\theta$2s) in cross section along the sagittal plane P2 is 20.5° to 23.0°, and preferably 21.0° to 22.0°, and the angle ($\theta$2f) in cross section along the coronal plane P3 is 1.5° to 6.5°, and preferably 2.5° to 5.5°.

Figure 9:
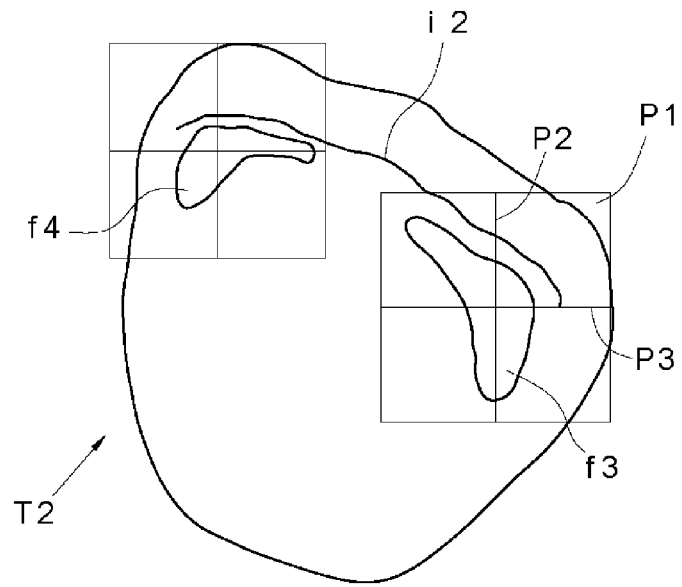
FIG. 9 is a view of an occlusal surface of an artificial tooth for maxillary lateral incisor.

FIG. 9 illustrates the artificial tooth for maxillary lateral incisor T2.

The artificial tooth for maxillary lateral incisor T2 has a protrusive facet f3 and a retrusive facet f4 on an incisal edge i2.

Of angles formed by the protrusive facet f3 with the occlusal plane P1, the angle in cross section along the sagittal plane P2 is 23.0° to 28.0°, and preferably 25.0° to 26.0°, and the angle in cross section along the coronal plane P3 is 15.0° to 17.0°, and preferably 15.5° to 16.5°.

Of angles formed by the retrusive facet f4 with the occlusal plane P1, the angle in cross section along the sagittal plane P2 is 16.0° to 22.0°, and preferably 17.0° to 20.0°, and the angle in cross section along the coronal plane P3 is 9.5° to 10.5°, and preferably 10.0° to 10.5°.

Figure 10:
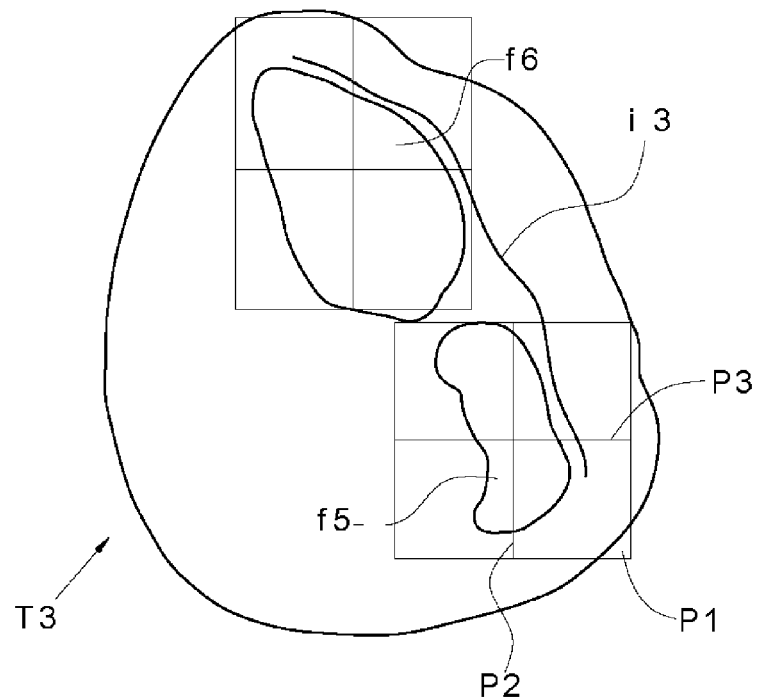
FIG. 10 is a view of an occlusal surface of an artificial tooth for maxillary canine.

FIG. 10 illustrates the artificial tooth for maxillary canine T3.

The artificial tooth for maxillary canine T3 has a protrusive facet f5 and a retrusive facet f6 on an incisal edge i3.

Of angles formed by the protrusive facet f5 with the occlusal plane P1, the angle in cross section along the sagittal plane P2 is 25.0° to 31.0°, and preferably 26.0° to 30.0°, and the angle in cross section along the coronal plane P3 is 1.5° to 5.0°, and preferably 2.5° to 4.5°.

Of angles formed by the retrusive facet f6 with the occlusal plane P1, the angle in cross section along the sagittal plane P2 is 8.5° to 22.5°, and preferably 10.0° to 15.0°, and the angle in cross section along the coronal plane P3 is 18.0° to 25.0°, and preferably 19.0° to 24.0°.

Figure 11:
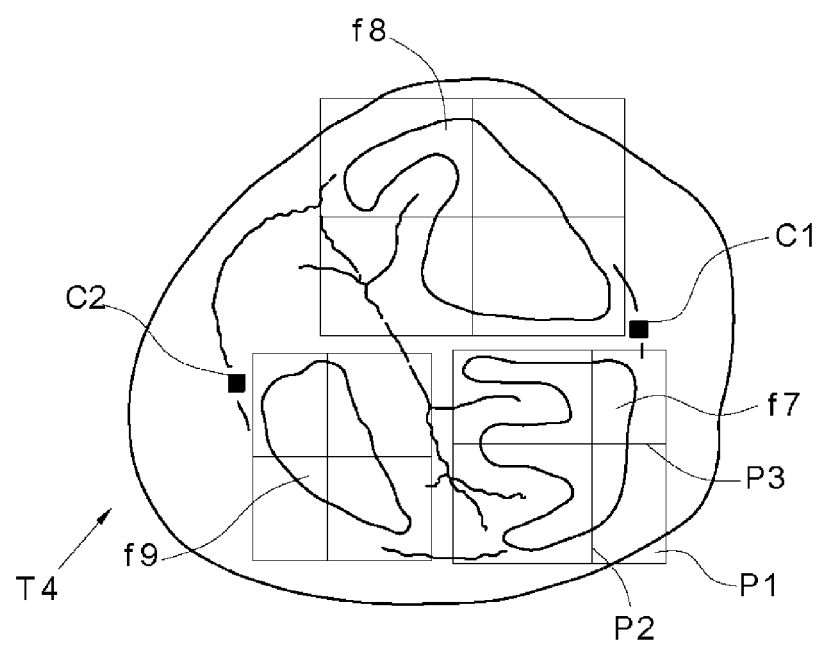
FIG. 11 is a view of an occlusal surface of an artificial tooth for maxillary first premolar.

FIG. 11 illustrates the artificial tooth for maxillary first premolar T4.

The artificial tooth for maxillary first premolar T4 has a protrusive facet f7 and a retrusive facet f8 near a buccal cusp apex c1, and a balancing facet f9 near a lingual cusp apex c2.

Of angles formed by the protrusive facet f7 with the occlusal plane P1, the angle in cross section along the sagittal plane P2 is 24.5° to 27.5°, and preferably 25.5° to 27.0°, and the angle in cross section along the coronal plane P3 is 8.5° to 16.4°, and preferably 10.0° to 15.0°.

Of angles formed by the retrusive facet f8 with the occlusal plane P1, the angle in cross section along the sagittal plane P2 is 18.5° to 27.0°, and preferably 20.5° to 25.0°, and the angle in cross section along the coronal plane P3 is 10.0° to 18.0°, and preferably 13.5° to 16.5°.

Of angles formed by the balancing facet f9 with the occlusal plane P1, the angle in cross section along the sagittal plane P2 is 1.5° to 4.5°, and preferably 2.0° to 3.5°, and the angle in cross section along the coronal plane P3 is 29.5° to 35.5°, and preferably 30.0° to 35.0°.

Figure 12:
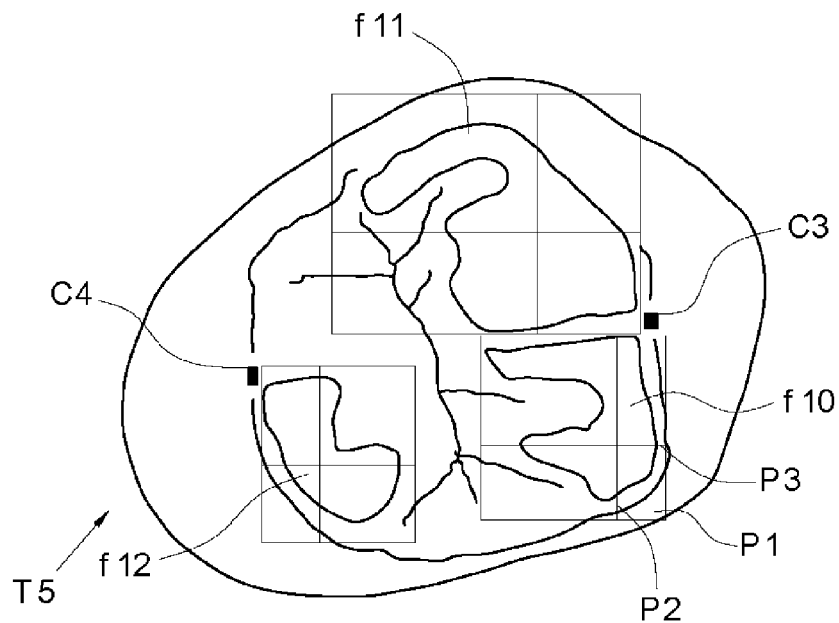
FIG. 12 is a view of an occlusal surface of an artificial tooth for maxillary second premolar.

FIG. 12 illustrates the artificial tooth for maxillary second premolar T5.

The artificial tooth for maxillary second premolar T5 has a protrusive facet f10 and a retrusive facet f11 near a buccal cusp apex c3, and a balancing facet f12 near a lingual cusp apex c4.

Of angles formed by the protrusive facet f10 with the occlusal plane P1, the angle in cross section along the sagittal plane P2 is 23.0° to 28.0°, and preferably 23.5° to 27.0°, and the angle in cross section along the coronal plane P3 is 10.0° to 19.0°, and preferably 12.5° to 15.5°.

Of angles formed by the retrusive facet f11 with the occlusal plane P1, the angle in cross section along the sagittal plane P2 is 16.5° to 19.0°, and preferably 17.5° to 18.5°, and the angle in cross section along the coronal plane P3 is 13.0° to 17.5°, and preferably 14.0° to 15.5°.

Of angles formed by the balancing facet f12 with the occlusal plane P1, the angle in cross section along the sagittal plane P2 is 6.0° to 10.0°, and preferably 7.5° to 9.0°, and the angle in cross section along the coronal plane P3 is 25.5° to 29.0°, and preferably 27.0° to 28.0°.

Figure 13:
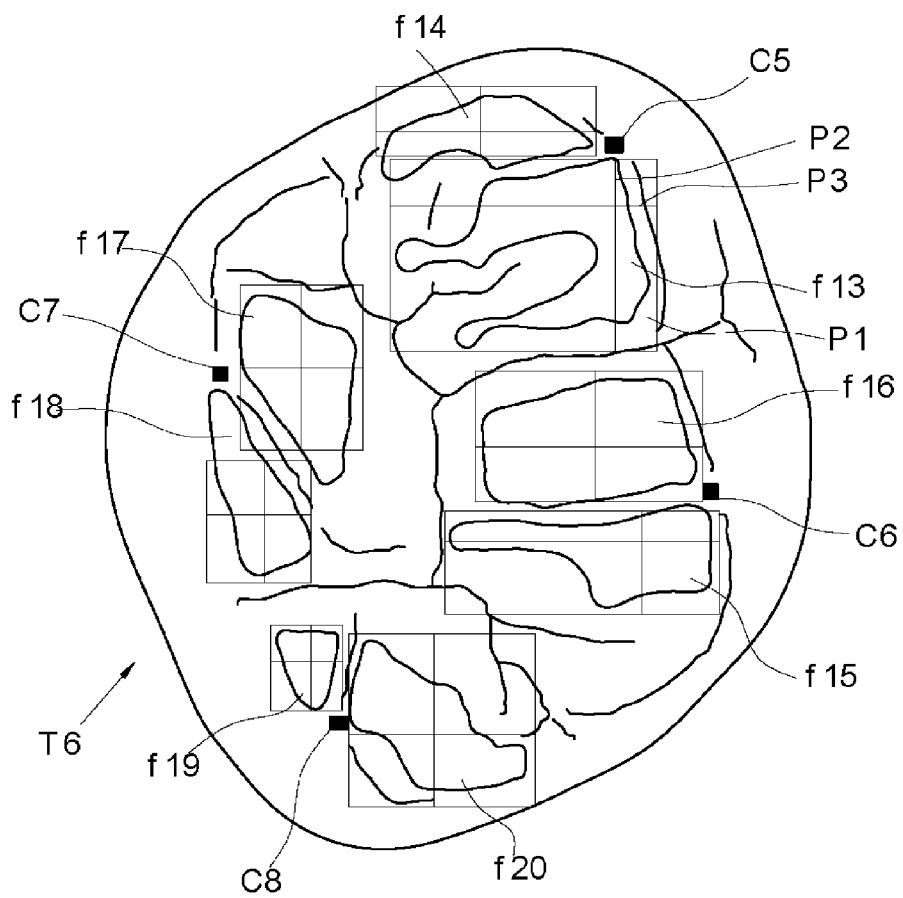
FIG. 13 is a view of an occlusal surface of an artificial tooth for maxillary first molar.

FIG. 13 illustrates the artificial tooth for maxillary first molar T6.

The artificial tooth for maxillary first molar T6 has a protrusive facet f13 and a retrusive facet f14 near a mesiobuccal cusp apex c5, and a protrusive facet f15 and a retrusive facet f16 near a distobuccal cusp apex c6. The artificial tooth for maxillary first molar T6 further has a balancing facet f17 and a protrusive facet f18 near a mesiolingual cusp apex c7, and a retrusive facet f19 and a balancing facet f20 near a distolingual cusp apex c8.

Of angles formed by the protrusive facet f13 with the occlusal plane P1, the angle in cross section along the sagittal plane P2 is 18.5° to 21.0°, and preferably 19.5° to 20.5°, and the angle in cross section along the coronal plane P3 is 5.0° to 11.0°, and preferably 6.0° to 10.0°.

Of angles formed by the retrusive facet f14 with the occlusal plane P1, the angle in cross section along the sagittal plane P2 is 7.0° to 12.0°, and preferably 7.5° to 10.0°, and the angle in cross section along the coronal plane P3 is 9.0° to 13.0°, and preferably 10.0° to 12.0°.

Of angles formed by the protrusive facet f15 with the occlusal plane P1, the angle in cross section along the sagittal plane P2 is 15.5° to 19.5°, and preferably 17.0° to 18.5°, and the angle in cross section along the coronal plane P3 is 8.0° to 9.0°, and preferably 8.5° to 9.0°.

Of angles formed by the retrusive facet f16 with the occlusal plane P1, the angle in cross section along the sagittal plane P2 is 18.5° to 23.0°, and preferably 19.0° to 21.0°, and the angle in cross section along the coronal plane P3 is 11.0° to 13.5°, and preferably 12.0° to 13.0°.

Of angles formed by the balancing facet f17 with the occlusal plane P1, the angle in cross section along the sagittal plane P2 is 14.5° to 16.5°, and preferably 15.0° to 16.0°, and the angle in cross section along the coronal plane P3 is 40.0° to 42.0°, and preferably 40.5° to 41.5°.

Of angles formed by the protrusive facet f18 with the occlusal plane P1, the angle in cross section along the sagittal plane P2 is 18.5° to 19.5°, and preferably 18.5° to 19.0°, and the angle in cross section along the coronal plane P3 is 4.5° to 6.5°, and preferably 5.0° to 6.0°.

Of angles formed by the retrusive facet f19 with the occlusal plane P1, the angle in cross section along the sagittal plane P2 is 6.5° to 7.5°, and preferably 7.0° to 7.5°, and the angle in cross section along the coronal plane P3 is 15.5° to 18.0°, and preferably 16.0° to 17.5°.

Of angles formed by the balancing facet f20 with the occlusal plane P1, the angle in cross section along the sagittal plane P2 is 3.0° to 12.0°, and preferably 5.0° to 10.0°, and the angle in cross section along the coronal plane P3 is 32.0° to 38.5°, and preferably 33.0° to 37.0°.

Figure 14:
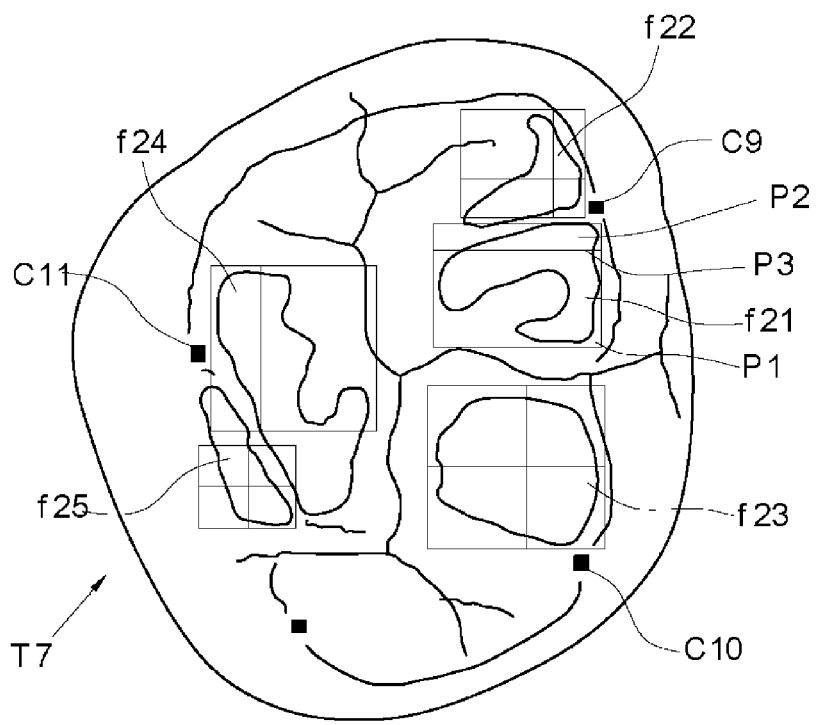
FIG. 14 is a view of an occlusal surface of an artificial tooth for maxillary second molar.

FIG. 14 illustrates the artificial tooth for maxillary second molar T7.

The artificial tooth for maxillary second molar T7 has a protrusive facet f21 and a retrusive facet f22 near a mesiobuccal cusp apex c9, and a retrusive facet f23 near a distobuccal cusp apex c10. The artificial tooth for maxillary second molar T7 further has a balancing facet f24 and a protrusive facet f25 near a mesiolingual cusp apex c11.

Of angles formed by the protrusive facet f21 with the occlusal plane P1, the angle in cross section along the sagittal plane P2 is 22.5° to 25.5°, and preferably 23.0° to 25.0°, and the angle in cross section along the coronal plane P3 is 1.0° to 2.5°, and preferably 1.5° to 2.0°.

Of angles formed by the retrusive facet f22 with the occlusal plane P1, the angle in cross section along the sagittal plane P2 is 9.5° to 17.5°, and preferably 10.0° to 15.0°, and the angle in cross section along the coronal plane P3 is 13.0° to 16.5°, and preferably 14.0° to 15.5°.

Of angles formed by the retrusive facet f23 with the occlusal plane P1, the angle in cross section along the sagittal plane P2 is 6.5° to 12.0°, and preferably 7.0° to 11.5°, and the angle in cross section along the coronal plane P3 is 4.5° to 7.0°, and preferably 5.0° to 6.5°.

Of angles formed by the balancing facet f24 with the occlusal plane P1, the angle in cross section along the sagittal plane P2 is 0.5° to 10.0°, and preferably 2.0° to 7.5°, and the angle in cross section along the coronal plane P3 is 38.5° to 47.0°, and preferably 39.0° to 45.0°.

Of angles formed by the protrusive facet f25 with the occlusal plane P1, the angle in cross section along the sagittal plane P2 is 20.5° to 22.5°, and preferably 21.0° to 22.0°, and the angle in cross section along the coronal plane P3 is 1.5° to 6.0°, and preferably 2.0° to 4.0°.

Figure 15:
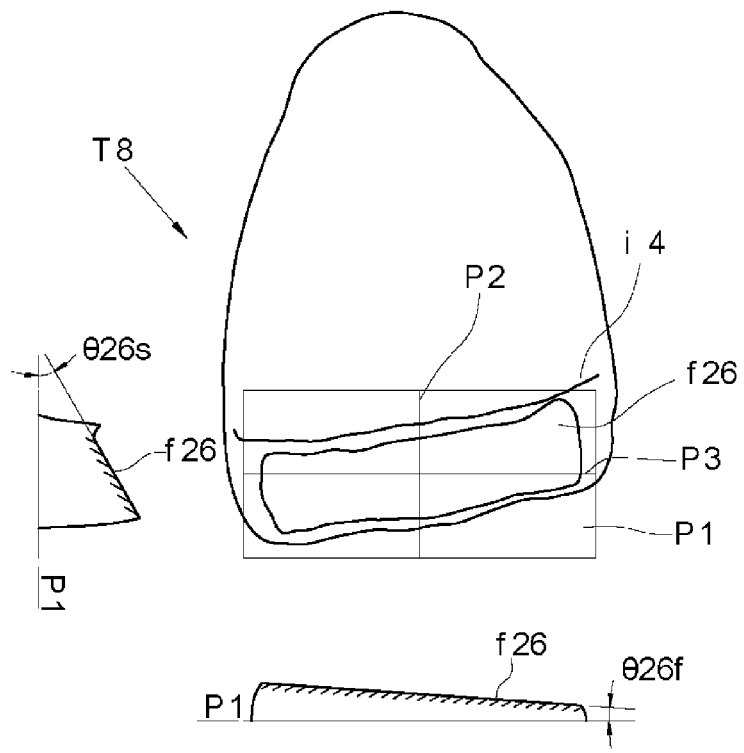
FIG. 15 is a view of an occlusal surface of an artificial tooth for mandibular central incisor.

FIG. 15 illustrates the artificial tooth for mandibular central incisor T8.

The artificial tooth for mandibular central incisor T8 has a protrusive facet f26 on an incisal edge i4.

Of angles formed by the protrusive facet f26 with the occlusal plane P1, the angle in cross section along the sagittal plane P2 ($\theta 26s$) is 27.0° to 35.0°, and preferably 28.0° to 33.5°, and the angle in cross section along the coronal plane P3 ($\theta 26f$) is 3.5° to 12.5°, and preferably 5.0° to 11.0°.

Figure 16:
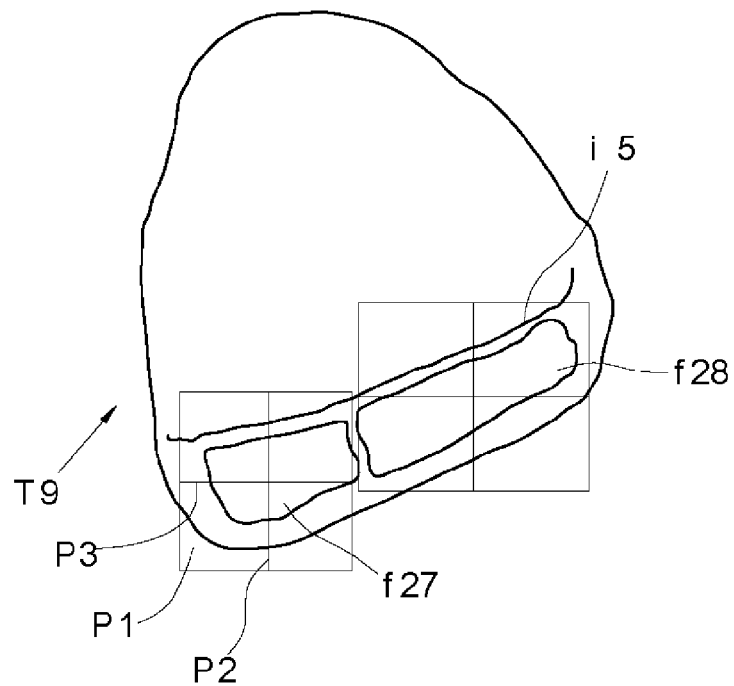
FIG. 16 is a view of an occlusal surface of an artificial tooth for mandibular lateral incisor.

FIG. 16 illustrates the artificial tooth for mandibular lateral incisor T9.

The artificial tooth for mandibular lateral incisor T9 has a protrusive facet f27 and a retrusive facet f28 on an incisal edge i5.

Of angles formed by the protrusive facet f27 with the occlusal plane P1, the angle in cross section along the sagittal plane P2 is 31.0° to 35.0°, and preferably 32.0° to 33.5°, and the angle in cross section along the coronal plane P3 is 0.0° to 1.5°, and preferably 0.5° to 1.0°.

Of angles formed by the retrusive facet f28 with the occlusal plane P1, the angle in cross section along the sagittal plane P2 is 22.0° to 35.0°, and preferably 23.0° to 30.5°, and the angle in cross section along the coronal plane P3 is 17.5° to 26.5°, and preferably 18.0° to 23.5°.

Figure 17:
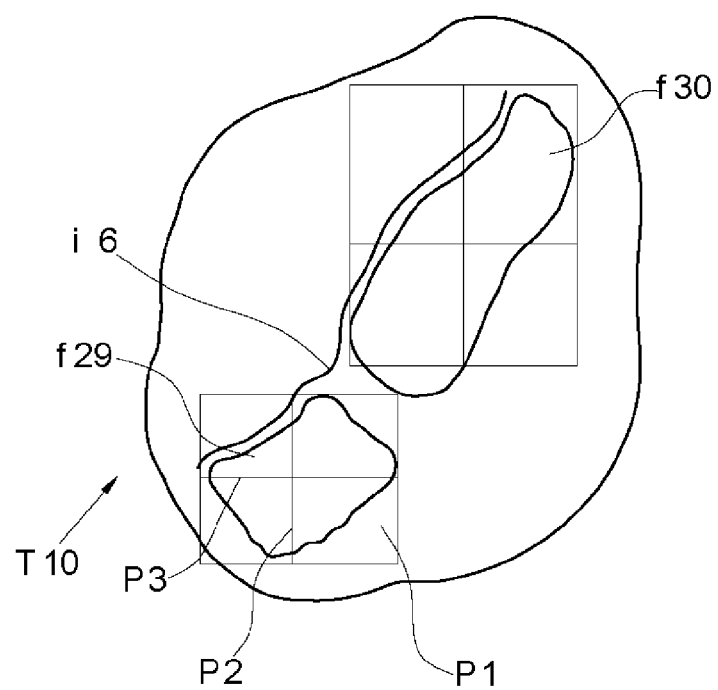
FIG. 17 is a view of an occlusal surface of an artificial tooth for mandibular canine.

FIG. 17 illustrates the artificial tooth for mandibular canine T10.

The artificial tooth for mandibular canine T10 has a protrusive facet f29 and a retrusive facet f30 on an incisal edge i6.

Of angles formed by the protrusive facet f29 with the occlusal plane P1, the angle in cross section along the sagittal plane P2 is 23.0° to 28.0°, and preferably 24.0° to 26.0°, and the angle in cross section along the coronal plane P3 is 0.5° to 10.0°, and preferably 2.5° to 8.0°.

Of angles formed by the retrusive facet f30 with the occlusal plane P1, the angle in cross section along the sagittal plane P2 is 14.5° to 18.0°, and preferably 15.0° to 16.5°, and the angle in cross section along the coronal plane P3 is 16.0° to 21.0°, and preferably 17.5° to 19.5°.

Figure 18:
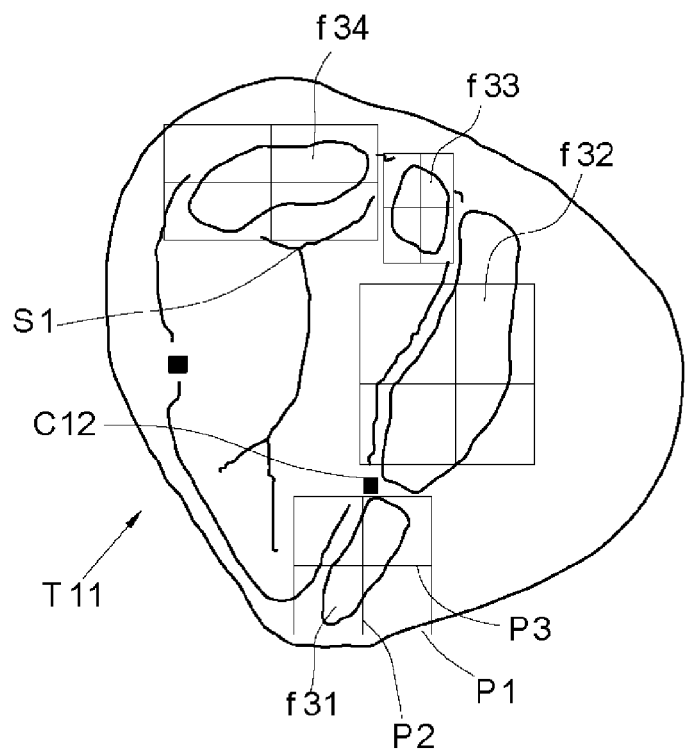
FIG. 18 is a view of an occlusal surface of an artificial tooth for mandibular first premolar.

FIG. 18 illustrates the artificial tooth for mandibular first premolar T11.

The artificial tooth for mandibular first premolar T11 has a protrusive facet f31 and a retrusive facet f32 around a buccal cusp apex c12, and a balancing facet f33 and a protrusive facet f34 near a distal fossette s1.

Of angles formed by the protrusive facet f31 with the occlusal plane P1, the angle in cross section along the sagittal plane P2 is 38.0° to 41.0°, and preferably 39.0° to 40.0°, and the angle in cross section along the coronal plane P3 is 5.0° to 8.5°, and preferably 6.0° to 7.5°.

Of angles formed by the retrusive facet f32 with the occlusal plane P1, the angle in cross section along the sagittal plane P2 is 7.0° to 17.5°, and preferably 10.0° to 15.0°, and the angle in cross section along the coronal plane P3 is 9.0° to 15.5°, and preferably 10.0° to 13.5°.

Of angles formed by the balancing facet f33 with the occlusal plane P1, the angle in cross section along the sagittal plane P2 is 15.0° to 24.0°, and preferably 16.0° to 23.0°, and the angle in cross section along the coronal plane P3 is 29.0° to 32.0°, and preferably 30.0° to 31.0°.

Of angles formed by the protrusive facet f34 with the occlusal plane P1, the angle in cross section along the sagittal plane P2 is 3.5° to 10.0°, and preferably 5.0° to 7.5°, and the angle in cross section along the coronal plane P3 is 1.0° to 5.0°, and preferably 2.5° to 4.5°.

Figure 19:
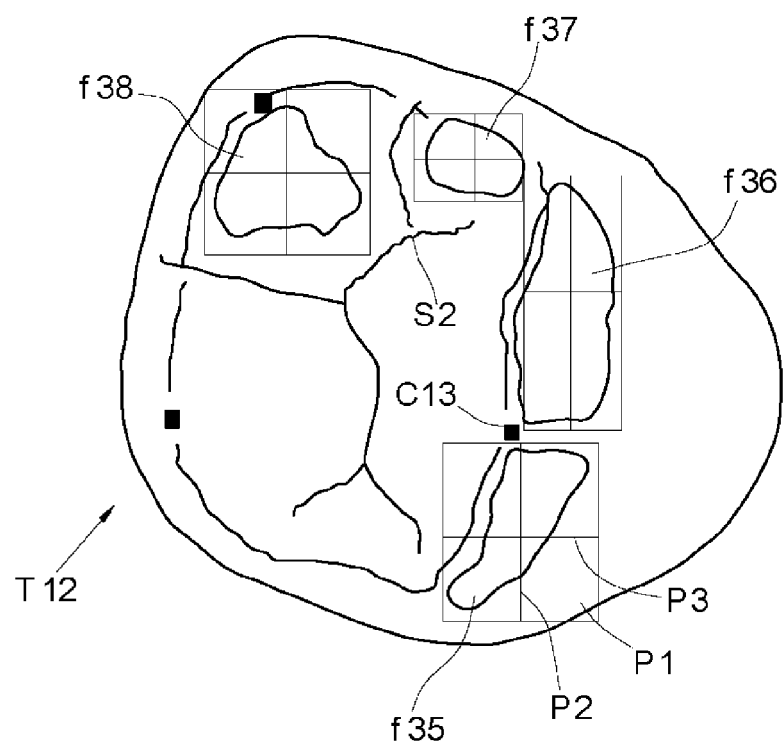
FIG. 19 is a view of an occlusal surface of an artificial tooth for mandibular second premolar.

FIG. 19 illustrates the artificial tooth for mandibular second premolar T12.

The artificial tooth for mandibular second premolar T12 has a protrusive facet f35 and a retrusive facet f36 around a buccal cusp apex c13, and a balancing facet f37 and a protrusive facet f38 near a distal fossette s2.

Of angles formed by the protrusive facet f35 with the occlusal plane P1, the angle in cross section along the sagittal plane P2 is 27.5° to 30.0°, and preferably 28.0° to 29.0°, and the angle in cross section along the coronal plane P3 is 16.0° to 19.0°, and preferably 17.5° to 18.5°.

Of angles formed by the retrusive facet f36 with the occlusal plane P1, the angle in cross section along the sagittal plane P2 is 13.0° to 15.0°, and preferably 13.5° to 14.5°, and the angle in cross section along the coronal plane P3 is 17.0° to 24.0°, and preferably 18.5° to 23.0°.

Of angles formed by the balancing facet f37 with the occlusal plane P1, the angle in cross section along the sagittal plane P2 is 1.5° to 17.0°, and preferably 15.5° to 16.5°, and the angle in cross section along the coronal plane P3 is 10.0° to 16.5°, and preferably 12.0° to 15.5°.

Of angles formed by the protrusive facet f38 with the occlusal plane P1, the angle in cross section along the sagittal plane P2 is 2.0° to 5.0°, and preferably 3.0° to 4.0°, and the angle in cross section along the coronal plane P3 is 12.0° to 14.5°, and preferably 12.5° to 13.5°.

Figure 20:
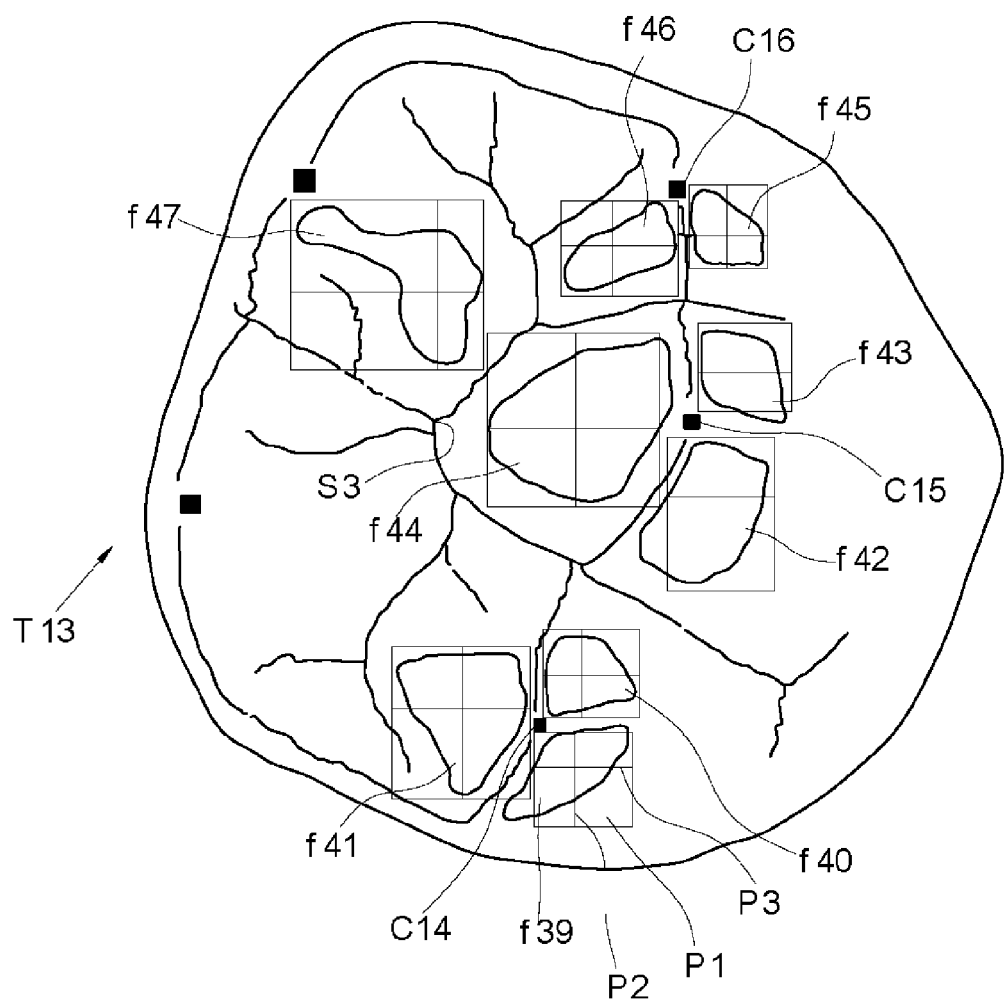
FIG. 20 is a view of an occlusal surface of an artificial tooth for mandibular first molar.

FIG. 20 illustrates the artificial tooth for mandibular first molar T13.

The artificial tooth for mandibular first molar T13 has a protrusive facet f39, a retrusive facet f40 and a balancing facet f41 around a mesiobuccal cusp apex c14, and a protrusive facet f42, a retrusive facet f43 and a balancing facet f44 around a distobuccal cusp apex c15. The artificial tooth for mandibular first molar T13 further has a protrusive facet f45 and a balancing facet f46 around a distal cusp apex c16, and a protrusive facet f47 near a central fossa s3.

Of angles formed by the protrusive facet f39 with the occlusal plane P1, the angle in cross section along the sagittal plane P2 is 23.5° to 32.0°, and preferably 25.0° to 30.0°, and the angle in cross section along the coronal plane P3 is 7.0° to 15.0°, and preferably 8.0° to 12.0°.

Of angles formed by the retrusive facet f40 with the occlusal plane P1, the angle in cross section along the sagittal plane P2 is 7.5° to 12.0°, and preferably 9.0° to 11.0°, and the angle in cross section along the coronal plane P3 is 14.0° to 16.0°, and preferably 14.5 to 15.5°.

Of angles formed by the balancing facet f41 with the occlusal plane P1, the angle in cross section along the sagittal plane P2 is 2.0° to 5.5°, and preferably 3.0° to 4.5°, and the angle in cross section along the coronal plane P3 is 30.0° to 32.0°, and preferably 30.0° to 31.5°.

Of angles formed by the protrusive facet f42 with the occlusal plane P1, the angle in cross section along the sagittal plane P2 is 15.5° to 21.0°, and preferably 16.0° to 19.0°, and the angle in cross section along the coronal plane P3 is 8.0° to 11.0°, and preferably 9.0° to 10.5°.

Of angles formed by the retrusive facet f43 with the occlusal plane P1, the angle in cross section along the sagittal plane P2 is 25.0° to 27.0°, and preferably 25.5° to 26.0°, and the angle in cross section along the coronal plane P3 is 24.0° to 25.0°, and preferably 24.5° to 25.0°.

Of angles formed by the balancing facet f44 with the occlusal plane P1, the angle in cross section along the sagittal plane P2 is 12.0° to 20.0°, and preferably 13.5° to 18.5°, and the angle in cross section along the coronal plane P3 is 30.0° to 37.0°, and preferably 31.5° to 33.5°.

Of angles formed by the protrusive facet f45 with the occlusal plane P1, the angle in cross section along the sagittal plane P2 is 7.5° to 13.0°, and preferably 9.0° to 11.5°, and the angle in cross section along the coronal plane P3 is 10.0° to 13.0°, and preferably 10.5° to 12.0°.

Of angles formed by the balancing facet f46 with the occlusal plane P1, the angle in cross section along the sagittal plane P2 is 2.5° to 4.5°, and preferably 3.0° to 4.0°, and the angle in cross section along the coronal plane P3 is 27.0° to 33.0°, and preferably 29.0° to 32.0°.

Of angles formed by the protrusive facet f47 with the occlusal plane P1, the angle in cross section along the sagittal plane P2 is 10.5° to 18.5°, and preferably 12.5° to 16.5°, and the angle in cross section along the coronal plane P3 is 1.0° to 8.0°, and preferably 2.5° to 6.0°.

Figure 21:
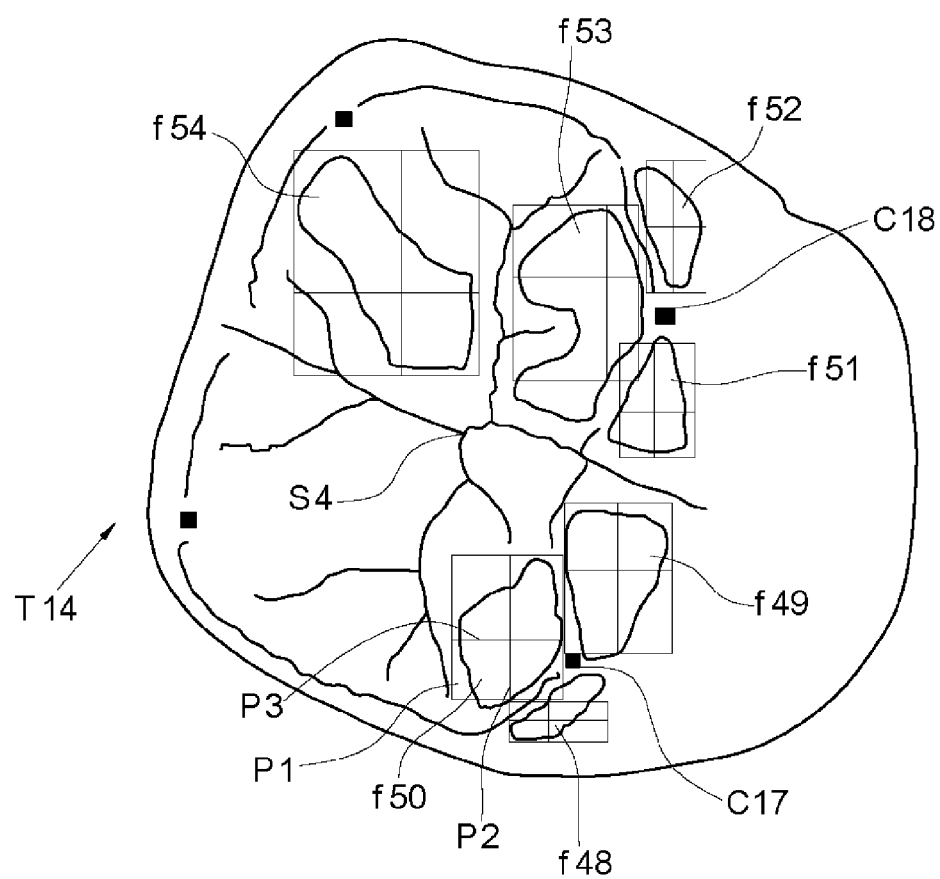
FIG. 21 is a view of an occlusal surface of an artificial tooth for mandibular second molar.

FIG. 21 illustrates the artificial tooth for mandibular second molar T14.

The artificial tooth for mandibular second molar T14 has a protrusive facet f48, a retrusive facet f49 and a balancing facet f50 around a mesiobuccal cusp apex c17. The artificial tooth for mandibular second molar T14 further has a protrusive facet f51, a retrusive facet f52 and a balancing facet f53 around a distobuccal cusp apex c18, and a protrusive facet f54 near a central fossa s4.

Of angles formed by the protrusive facet f48 with the occlusal plane P1, the angle in cross section along the sagittal plane P2 is 26.0° to 30.0°, and preferably 27.0° to 29.0°, and the angle in cross section along the coronal plane P3 is 10.0° to 13.0°, and preferably 10.5° to 12.5°.

Of angles formed by the retrusive facet f49 with the occlusal plane P1, the angle in cross section along the sagittal plane P2 is 14.0° to 16.0°, and preferably 14.5° to 15.5°, and the angle in cross section along the coronal plane P3 is 15.0° to 17.5°, and preferably 15.5 to 17.0°.

Of angles formed by the balancing facet f50 with the occlusal plane P1, the angle in cross section along the sagittal plane P2 is 2.5° to 3.5°, and preferably 2.5° to 3.0°, and the angle in cross section along the coronal plane P3 is 34.0° to 38.0°, and preferably 35.0° to 37.0°.

Of angles formed by the protrusive facet f51 with the occlusal plane P1, the angle in cross section along the sagittal plane P2 is 17.0° to 21.0°, and preferably 18.0° to 20.0°, and the angle in cross section along the coronal plane P3 is 4.5° to 6.5°, and preferably 5.0° to 6.0°.

Of angles formed by the retrusive facet f52 with the occlusal plane P1, the angle in cross section along the sagittal plane P2 is 19.0° to 22.0°, and preferably 19.5° to 21.0°, and the angle in cross section along the coronal plane P3 is 13.0° to 14.5°, and preferably 13.5° to 14.0°.

Of angles formed by the balancing facet f53 with the occlusal plane P1, the angle in cross section along the sagittal plane P2 is 1.0° to 3.0°, and preferably 1.5° to 2.5°, and the angle in cross section along the coronal plane P3 is 34.0° to 38.0°, and preferably 35.0° to 37.0°.

Of angles formed by the protrusive facet f54 with the occlusal plane P1, the angle in cross section along the sagittal plane P2 is 15.5° to 23.0°, and preferably 17.0° to 20.0°, and the angle in cross section along the coronal plane P3 is 5.5° to 12.0°, and preferably 7.0° to 10.0°.

Figure 22:
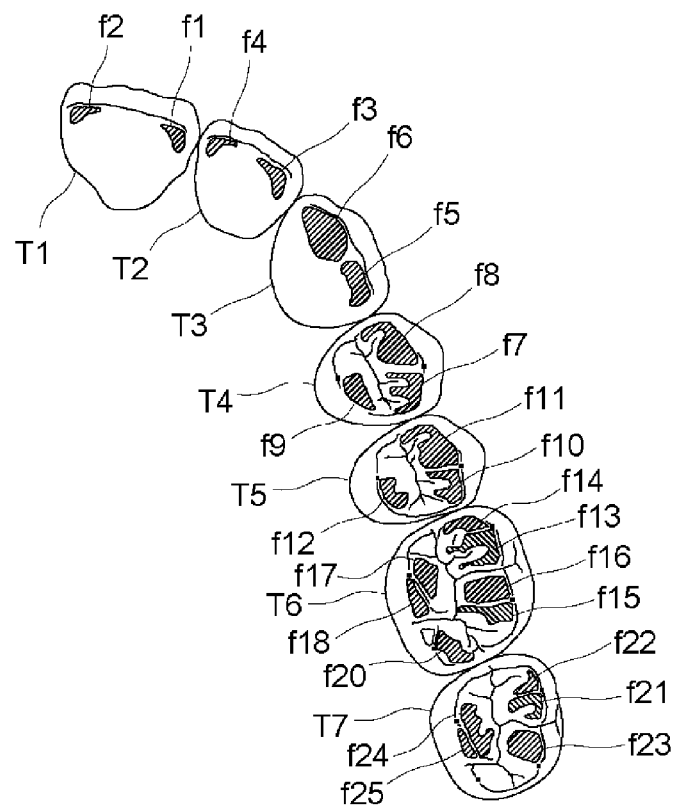
FIG. 22 is a view of a set of artificial teeth illustrating occlusal facets thereof that partially make contact in intercuspation.
Figure 22:
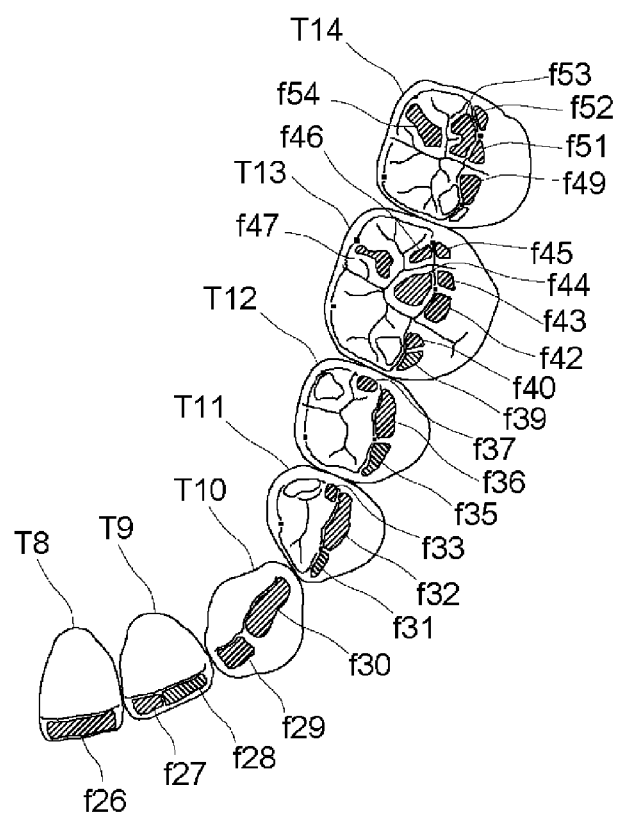

When the maxillary artificial teeth and the mandibular artificial teeth respectively having the occlusal facets described so far are set in a mean value articulator, the occlusal facets make the following contacts in intercuspation as illustrated in FIG. 22.

The protrusive facet f1 of the artificial tooth for maxillary central incisor T1 partially contacts the protrusive facet f27 of the artificial tooth for mandibular lateral incisor T9.

The retrusive facet f2 of the artificial tooth for maxillary central incisor T1 partially contacts the protrusive facet f26 of the artificial tooth for mandibular central incisor T8.

The protrusive facet f3 of the artificial tooth for maxillary lateral incisor T2 partially contacts the protrusive facet f29 of the artificial tooth for mandibular canine T10.

The retrusive facet f4 of the artificial tooth for maxillary lateral incisor T2 partially contacts the retrusive facet f28 of the artificial tooth for mandibular lateral incisor T9.

The protrusive facet f5 of the artificial tooth for maxillary canine T3 partially contacts the protrusive facet f31 of the artificial tooth for mandibular first premolar T11.

The retrusive facet f6 of the artificial tooth for maxillary canine T3 partially contacts the retrusive facet f30 of the artificial tooth for mandibular canine T10.

The protrusive facet f7 of the artificial tooth for maxillary first premolar T4 partially contacts the protrusive facet f35 of the artificial tooth for mandibular second premolar T12.

The retrusive facet f8 of the artificial tooth for maxillary first premolar T4 partially contacts the retrusive facet f32 of the artificial tooth for mandibular first premolar T11.

The balancing facet f9 of the artificial tooth for maxillary first premolar T4 partially contacts the balancing facet f33 of the artificial tooth for mandibular first premolar T11.

The protrusive facet f10 of the artificial tooth for maxillary second premolar T5 partially contacts the protrusive facet f39 of the artificial tooth for mandibular first molar T13.

The retrusive facet f11 of the artificial tooth for maxillary second premolar T5 partially contacts the retrusive facet f36 of the artificial tooth for mandibular second premolar T12.

The balancing facet f12 of the artificial tooth for maxillary second premolar T5 partially contacts the balancing facet f37 of the artificial tooth for mandibular second premolar T12.

The protrusive facet f13 of the artificial tooth for maxillary first molar T6 partially contacts the protrusive facet f42 of the artificial tooth for mandibular first molar T13.

The retrusive facet f14 of the artificial tooth for maxillary first molar T6 partially contacts the retrusive facet f40 of the artificial tooth for mandibular first molar T13.

The protrusive facet f15 of the artificial tooth for maxillary first molar T6 partially contacts the protrusive facet f45 of the artificial tooth for mandibular first molar T13.

The retrusive facet f16 of the artificial tooth for maxillary first molar T6 partially contacts the retrusive facet f43 of the artificial tooth for mandibular first molar T13.

The balancing facet f17 of the artificial tooth for maxillary first molar T6 partially contacts the balancing facet f44 of the artificial tooth for mandibular first molar T13.

The protrusive facet f18 of the artificial tooth for maxillary first molar T6 partially contacts the protrusive facet f47 of the artificial tooth for mandibular first molar T13.

The balancing facet f20 of the artificial tooth for maxillary first molar T6 partially contacts the balancing facet f46 of the artificial tooth for mandibular first molar T13.

The protrusive facet f21 of the artificial tooth for maxillary second molar T7 partially contacts the protrusive facet f51 of the artificial tooth for mandibular second molar T14.

The retrusive facet f22 of the artificial tooth for maxillary second molar T7 partially contacts the retrusive facet f49 of the artificial tooth for mandibular second molar T14.

The retrusive facet f23 of the artificial tooth for maxillary second molar T7 partially contacts the retrusive facet f52 of the artificial tooth for mandibular second molar T14.

The balancing facet f24 of the artificial tooth for maxillary second molar T7 partially contacts the balancing facet f53 of the artificial tooth for mandibular second molar T14.

The protrusive facet f25 of the artificial tooth for maxillary second molar T7 partially contacts the protrusive facet f54 of the artificial tooth for mandibular second molar T14.

Below are described the gliding motility of the occlusal facets on the working and balancing sides in the protrusive and lateral movements.

Figure 23:
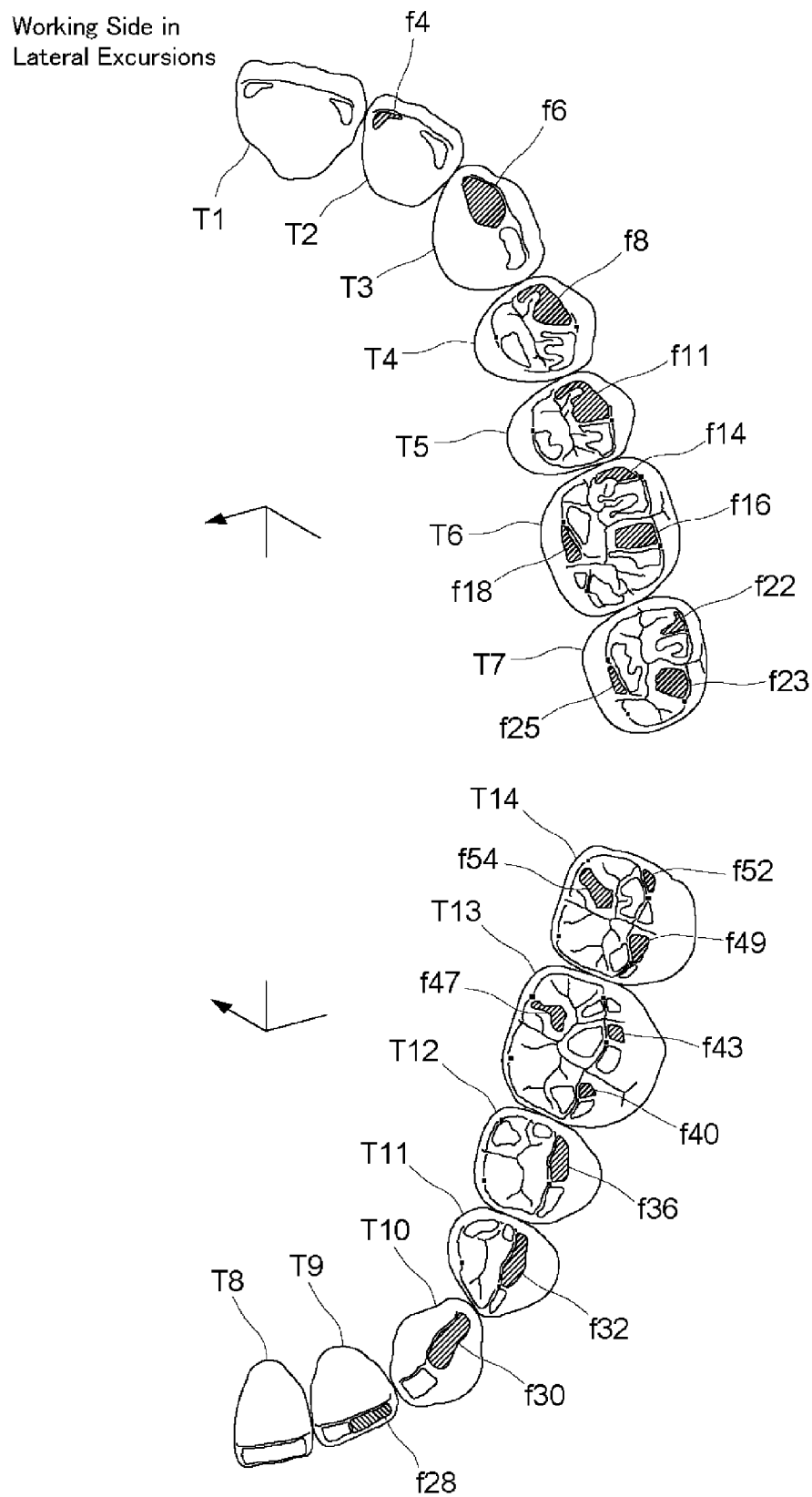
FIG. 23 is a view of a set of artificial teeth illustrating occlusal facets thereof that glide toward a working side in lateral, movements.

As illustrated in FIG. 23, the gliding motility on the working side in the lateral movements is as follows.

The retrusive facet f4 of the artificial tooth for maxillary lateral incisor T2 partially glides along the retrusive facet f28 of the artificial tooth for mandibular lateral incisor T9.

The retrusive facet f6 of the artificial tooth for maxillary canine T3 partially glides along the retrusive facet f30 of the artificial tooth for mandibular canine T10.

The retrusive facet f8 of the artificial tooth for maxillary first premolar T4 partially glides along the retrusive facet f32 of the artificial tooth for mandibular first premolar T11.

The retrusive facet f11 of the artificial tooth for maxillary second premolar T5 partially glides along the retrusive facet f36 of the artificial tooth for mandibular second premolar T12.

The retrusive facet f14 of the artificial tooth for maxillary first molar T6 partially glides along the retrusive facet f40 of the artificial tooth for mandibular first molar T13.

The retrusive facet f16 of the artificial tooth for maxillary first molar T6 partially glides along the retrusive facet f43 of the artificial tooth for mandibular first molar T13.

The protrusive facet f18 of the artificial tooth for maxillary first molar T6 partially glides along the protrusive facet f47 of the artificial tooth for mandibular first molar T13.

The retrusive facet f22 of the artificial tooth for maxillary second molar T7 partially glides along the retrusive facet f49 of the artificial tooth for mandibular second molar T14.

The retrusive facet f23 of the artificial tooth for maxillary second molar T7 partially glides along the retrusive facet f52 of the artificial tooth for mandibular second molar T14.

The protrusive facet f25 of the artificial tooth for maxillary second molar T7 partially glides along the protrusive facet f54 of the artificial tooth for mandibular second molar T14.

Figure 24:
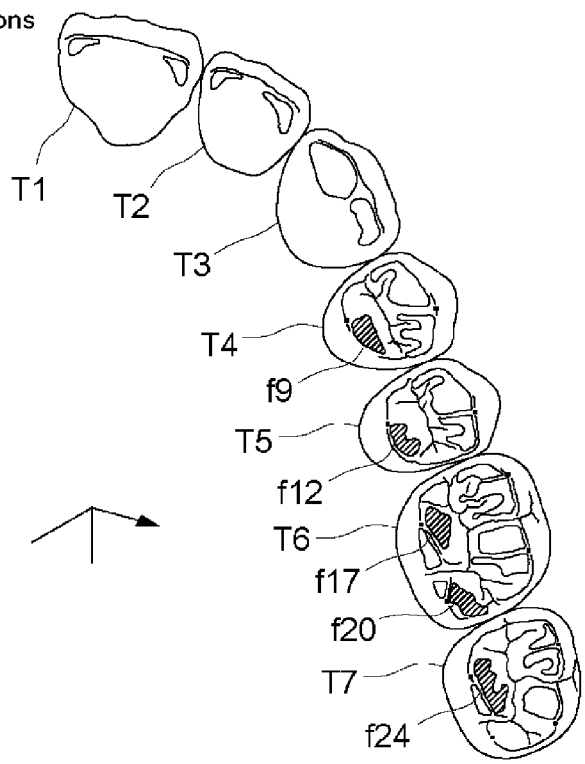
FIG. 24 is a view of a set of artificial teeth illustrating occlusal facets thereof that glide toward a balancing side in lateral excursions.
Figure 24:
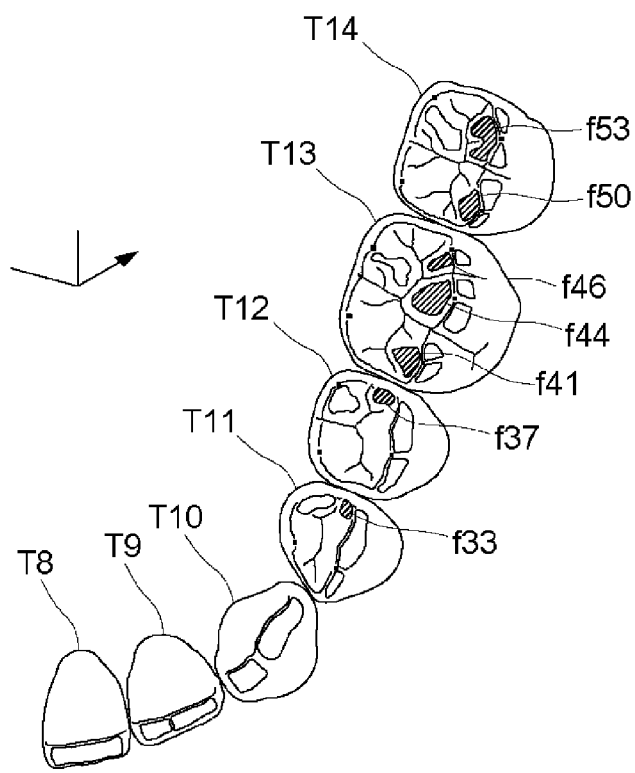

As illustrated in FIG. 24, the gliding motility on the balancing side in the lateral movements is as follows.

The balancing facet f9 of the artificial tooth for maxillary first premolar T4 partially glides along the balancing facet f33 of the artificial tooth for mandibular first premolar T11.

The balancing facet f12 of the artificial tooth for maxillary second premolar T5 partially glides along the balancing facet f37 of the artificial tooth for mandibular second premolar T12 and the balancing facet f41 of the artificial tooth for mandibular first molar T13.

The balancing facet f17 of the artificial tooth for maxillary first molar T6 partially glides along the balancing facet f44 of the artificial tooth for mandibular first molar T13.

The balancing facet f20 of the artificial tooth for maxillary first molar T6 partially glides along the balancing facet f46 of the artificial tooth for mandibular first molar T13 and the balancing facet f50 of the artificial tooth for mandibular second molar T14.

The balancing facet f24 of the artificial tooth for maxillary second molar T7 partially glides along the balancing facet f53 of the artificial tooth for mandibular second molar T14.

Figure 25:
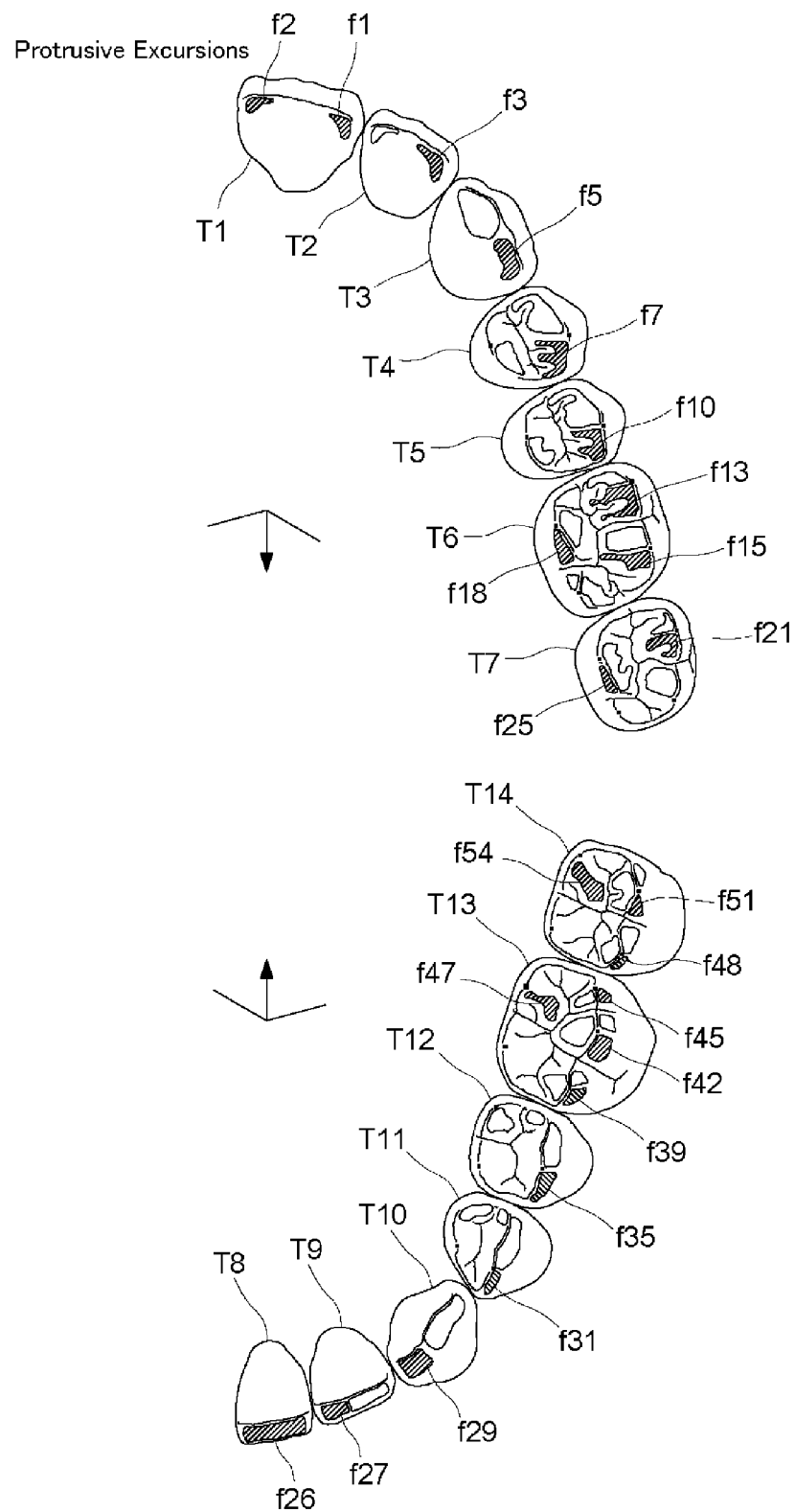
FIG. 25 is a view of a set of artificial teeth illustrating occlusal facets thereof that glide in protrusive movements.

As illustrated in FIG. 25, the gliding motility in the protrusive movements is as follows.

The protrusive facet f1 of the artificial tooth for maxillary central incisor T1 partially glides along the protrusive facet f27 of the artificial tooth for mandibular lateral incisor T9.

The retrusive facet f2 of the artificial tooth for maxillary central incisor T1 partially glides along the protrusive facet f26 of the artificial tooth for mandibular central incisor T8.

The protrusive facet f3 of the artificial tooth for maxillary lateral incisor T2 partially glides along the protrusive facet f29 of the artificial tooth for mandibular canine T10.

The protrusive facet f5 of the artificial tooth for maxillary canine T3 partially glides along the protrusive facet f31 of the artificial tooth for mandibular first premolar T11.

The protrusive facet f7 of the artificial tooth for maxillary first premolar T4 partially glides along the protrusive facet f35 of the artificial tooth for mandibular second premolar T12.

The protrusive facet f10 of the artificial tooth for maxillary second premolar T5 partially glides along the protrusive facet f39 of the artificial tooth for mandibular first molar T13.

The protrusive facet f13 of the artificial tooth for maxillary first molar T6 partially glides along the protrusive facet f42 of the artificial tooth for mandibular first molar T13.

The protrusive facet f15 of the artificial tooth for maxillary first molar T6 partially glides along the protrusive facet f45 of the artificial tooth for mandibular first molar T13 and the protrusive facet f48 of the artificial tooth for mandibular second molar T14.

The balancing facet f18 of the artificial tooth for maxillary first molar T6 partially glides along the protrusive facet f47 of the artificial tooth for mandibular first molar T13.

The protrusive facet f21 of the artificial tooth for maxillary second molar T7 partially glides along the protrusive facet f51 of the artificial tooth for mandibular second molar T14.

The protrusive facet f25 of the artificial tooth for maxillary second molar T7 partially glides along the protrusive facet f54 of the artificial tooth for mandibular second molar T14.

Examples of a material used for the artificial teeth according to the present preferred embodiment are ceramic materials such as feldspar, quarts and silica, and resin materials conventionally used in the field of odontologistry such as composite resin including a resin component, for example, MMA, UDMA, EDMA or Bis-GMA and an organic or inorganic filler, and acrylic resin. Any of these materials is suitably selected.

In the production of the artificial tooth, it is desirable to separately form a plurality of layers using materials having at least two different color tones respective for enamel and dentine layers and multilayer them to improve an aesthetic impression. Any of the foregoing materials is suitably selected. The two layers respectively having different color tones may be made of either a single material or two different materials differently colored beforehand.

The molding method can be suitably selected from compression molding, injection molding, and injection and compression molding.

The artificial teeth described so far are characterized in that the angles formed by the occlusal facets thereof with the occlusal plane of the mean value articulator were suitably set in advance so that the occlusal relation, generally called bilateral balanced occlusion, is retained. When the artificial teeth according to the present invention are used in the mean value articulator, a denture in a constant occlusal state can be effectively produced in a short period of time with less work in occlusal adjustments.

EXAMPLES

Below are described examples.

Nine dental technicians engaged in the alignment of artificial teeth were selected as their routine task for an alignment test of sample artificial teeth according to the present invention using Handy IIA articulator supplied by SHOFU INC. loaded with a toothless plaster model. Table 1 shows required time and objective evaluation on achievement of "bilateral balanced occlusion", and their own subjective evaluation on "if they found it easy to obtain the bilateral balanced occlusion".

TABLE 1

|  | Required time (min) | Achievement | Subjective evaluation |
|---|---|---|---|
| Dental technician A | 45 | Δ | ○ |
| Dental technician B | 43 | ○ | ○ |
| Dental technician C | 42 | ○ | ○ |
| Dental technician D | 88 | Δ | ○ |
| Dental technician E | 46 | Δ | x |
| Dental technician F | 35 | ○ | ○ |
| Dental technician G | 40 | ○ | ○ |

TABLE 1-continued

| | Required time (min) | Achievement | Subjective evaluation |
|---|---|---|---|
| Dental technician H | 37 | ○ | ○ |
| Dental technician I | 46 | ○ | ○ |

INDUSTRIAL APPLICABILITY

The present invention relates to artificial teeth used in a denture having a base plate produced by an odontologist or a dental technician for prosthodontic treatment.

An artificial tooth is an industrial product ranging in different designs and sizes, and the odontologist or dental technician chooses any suitable tooth from the available products.

The artificial teeth according to the present invention can be used for education, for example, practical trainings for students in learning teeth alignment and occlusal adjustment.

The invention claimed is:

1. A set of artificial teeth comprising:
an artificial tooth for maxillary first premolar (T4) having
two facets, a protrusive facet (f7) and a retrusive facet (f8), situated around a buccal cusp apex (C1), and
one facet, a balancing facet (f9), situated around a lingual cusp apex (C2),
wherein, of angles formed by the protrusive facet (f7) near the buccal cusp apex (C1) with an occlusal plane (P1), the angle in cross section along a sagittal plane (P2) is 24.5° to 27.5°, and the angle in cross section along a coronal plane (P3) is 8.5° to 16.4°,
wherein, of angles formed by the retrusive facet (f8) near the buccal cusp apex (C1) with the occlusal plane (P1), the angle in cross section along the sagittal plane (P2) is 18.5° to 27.0°, and the angle in cross section along the coronal plane is 10.0° to 18.0°, and
wherein, of angles formed by the balancing facet (f9) near the lingual cusp apex (C2) with the occlusal plane(P1), the angle in cross section along the sagittal plane (P2) is 1.5° to 4.5°, and the angle in cross section along the coronal plane (P3) is 29.5° to 35.5°; and
an artificial tooth for mandibular first premolar (T11) having
two facets, a protrusive facet (f31) and a retrusive facet (f32), situated around a buccal cusp apex (C12),
one facet, a balancing facet (f33), situated along a distal marginal ridge, and
one facet, a protrusive facet (f34), situated around a lingual cusp apex,
wherein, of angles formed by the protrusive facet (f31) near the buccal cusp apex (C12) with the occlusal plane (P1), the angle in cross section along the sagittal plane (P2) is 38.0° to 41.0°, and the angle in cross section along the coronal plane (P3) is 5.0° to 8.5°,
wherein, of angles formed by the retrusive facet (f32) near the buccal cusp apex (C12) with the occlusal plane (P1), the angle in cross section along the sagittal plane (P2) is 7.0° to 17.5°, and the angle in cross section along the coronal plane (P3) is 9.0° to 15.5°,
wherein, of angles formed by the balancing facet (f33) near the distal marginal ridge with the occlusal plane (P1), the angle in cross section along the sagittal plane (P2) is 15.0° to 24.0°, and the angle in cross section along the coronal plane (P3) is 29.0° to 32.0°, and
wherein, of angles formed by the protrusive facet (f34) near the lingual cusp apex with the occlusal plane (P1), the angle in cross section along the sagittal plane (P2) is 3.5° to 10.0°, and the angle in cross section along the coronal plane (P3) is 1.0° to 5.0°;
wherein the facets make the following contacts in intercuspation,
the retrusive facet (f8) of the artificial tooth for maxillary first premolar (T4) contacts the retrusive facet (f32) of the artificial tooth for mandibular first premolar (T11), and
the balancing facet (f9) of the artificial tooth for maxillary first premolar (T4) contacts the balancing facet (f33) of the artificial tooth for mandibular first premolar (T11);
wherein the facets have the following gliding motility when functioning as a working side in lateral movements,
the retrusive facet (f8) of the artificial tooth for maxillary first premolar (T4) glides along the retrusive facet (f32) of the artificial tooth for mandibular first premolar (T11); and
wherein, the facets have the following gliding motility when functioning as a balancing side in lateral movements,
the balancing facet (f9) of the artificial tooth for maxillary first premolar (T4) glides along the balancing facet (f33) of the artificial tooth for mandibular first premolar (T11).

2. A set of artificial teeth comprising:
an artificial tooth for maxillary second premolar (T5) having
two facets, a protrusive facet (f10) and a retrusive facet (f11), situated around a buccal cusp apex (C3), and
one facet, a balancing facet (f12), situated around a lingual cusp apex (C4),
wherein, of angles formed by the protrusive facet (f10) near the buccal cusp apex (C3) with an occlusal plane (P1), the angle in cross section along a sagittal plane (P2) is 23.0° to 28.0°, and the angle in cross section along a coronal plane (P3) is 10.0° to 19.0°,
wherein, of angles formed by the retrusive facet (f11) near the buccal cusp apex (C3) with the occlusal plane (P1), the angle in cross section along the sagittal plane (P2) is 16.5° to 19.0°, and the angle in cross section along the coronal plane (P3) is 13.0° to 17.5°, and
wherein, of angles formed by the balancing facet (f12) near the lingual cusp apex (C4) with the occlusal plane (P1), the angle in cross section along the sagittal plane (P2) is 6.0° to 10.0°, and the angle in cross section along the coronal plane (P3) is 25.5° to 29.0°; and
an artificial tooth for mandibular second premolar (T12) having
two facets, a protrusive facet (f35) and a retrusive facet (f36), situated around a buccal cusp apex (C13),
one facet, a balancing facet (f37), situated along a distal marginal ridge, and
one facet, a protrusive facet (f38), situated around a lingual cusp apex,
wherein, of angles formed by the protrusive facet (f35) near the buccal cusp apex (C13) with the occlusal plane (P1), the angle in cross section along the sagittal plane (P2) is 27.5° to 30.0°, and the angle in cross section along the coronal plane (P3) is 16.0° to 19.0°,
wherein, of angles formed by the retrusive facet (f36) near the buccal cusp apex (C13) with the occlusal plane (P1), the angle in cross section along the sagittal plane (P2) is 13.0° to 15.0°, and the angle in cross section along the coronal plane (P3) is 17.0° to 24.0°, wherein, of angles formed by the balancing facet (f37) near the distal marginal ridge with the occlusal plane (P1), the angle in cross section along the sagittal plane (P2) is 1.5° to 17.0°, and the angle in cross section along the coronal plane (P3) is 10.0° to 16.5°, and wherein, of angles formed by the protrusive facet (f38) near the lingual cusp apex with the occlusal plane (P1), the angle in cross section along the sagittal plane (P2) is 2.0° to 5.0°, and the angle in cross section along the coronal plane (P3) is 12.0° to 14.5°;

wherein the facets make the following contacts in intercuspation,
the retrusive facet (f11) of the artificial tooth for maxillary second premolar (T5) contacts the retrusive facet (f36) of the artificial tooth for mandibular second premolar (T12), and
the balancing facet (f12) of the artificial tooth for maxillary second premolar (T5) contacts the balancing facet (f37) of the artificial tooth for mandibular second premolar (T12);

wherein the facets have the following gliding motility when functioning as a working side in lateral movements,
the retrusive facet (f11) of the artificial tooth for maxillary second premolar (T5) glides along the retrusive facet (f36) of the artificial tooth for mandibular second premolar (T12); and wherein the facets have the following gliding motility when functioning as a balancing side in lateral movements, the balancing facet (f12) of the artificial tooth for maxillary second premolar (T5) glides along the balancing facet (f37) of the artificial tooth for mandibular second premolar (T12).

3. A set of artificial teeth comprising:
an artificial tooth for maxillary first molar (T6) having
two facets, a protrusive facet (f13) and a retrusive facet (f14), situated around a mesiobuccal cusp apex (C5),
two facets, a protrusive facet (f15) and a retrusive facet (f16), situated around a distobuccal cusp apex (C6),
two facets, a protrusive facet (f18) and a balancing facet (f17), situated around a mesiolingual cusp apex (C7), and
two facets, a retrusive facet (f19) and a balancing facet (f20), situated around a distolingual cusp apex (C8),
wherein, of angles formed by the protrusive facet (f13) near the mesiobuccal cusp apex (C5) with an occlusal plane (P1), the angle in cross section along a sagittal plane (P2) is 18.5° to 21.0°, and the angle in cross section along a coronal plane (P3) is 5.0° to 11.0°,
wherein, of angles formed by the retrusive facet (f14) near the mesiobuccal cusp apex (C5) with the occlusal plane (P1), the angle in cross section along the sagittal plane (P2) is 7.0° to 12.0°, and the angle in cross section along the coronal plane (P3) is 9.0° to 13.0°,
wherein, of angles formed by the protrusive facet (f15) near the distobuccal cusp apex (C6) with the occlusal plane (P1), the angle in cross section along the sagittal plane (P2) is 15.5° to 19.5°, and the angle in cross section along the coronal plane (P3) is 8.0° to 9.0°,
wherein, of angles formed by the retrusive facet (f16) near the distobuccal cusp apex (C6) with the occlusal plane (P1), the angle in cross section along the sagittal plane (P2) is 18.5° to 23.0°, and the angle in cross section along the coronal plane (P3) is 11.0° to 13.5°, wherein, of angles formed by the balancing facet (f17) near the mesiolingual cusp apex (C7) with the occlusal plane (P1), the angle in cross section along the sagittal plane (P2) is 14.5° to 16.5°, and the angle in cross section along the coronal plane (P3) is 40.0° to 42.0°, wherein, of angles formed by the protrusive facet (f18) near the mesiolingual cusp apex (C7) with the occlusal plane (P1), the angle in cross section along the sagittal plane (P2) is 18.5° to 19.5°, and the angle in cross section along the coronal plane (P3) is 4.5° to 6.5°, wherein, of angles formed by the retrusive facet (f19) near the distolingual cusp apex (C8) with the occlusal plane (P1), the angle in cross section along the sagittal plane (P2) is 6.5° to 7.5°, and the angle in cross section along the coronal plane (P3) is 15.5° to 18.0°, and wherein, of angles formed by the balancing facet (f20) near the distolingual cusp apex (C8) with the occlusal plane (P1), the angle in cross section along the sagittal plane (P2) is 3.0° to 12.0°, and the angle in cross section along the coronal plane (P3) is 32.0° to 38.5°; and an artificial tooth for mandibular first molar (T13) having
three facets, a protrusive facet (f39), a retrusive facet (f40) and a balancing facet (f41), situated around a mesiobuccal cusp apex (C14),
three facets, a protrusive facet (f42), a retrusive facet (f43) and a balancing facet (f44), situated around a distobuccal cusp apex (C15),
two facets, a protrusive facet (f45) and a balancing facet (f46), situated around a distal cusp apex (C16), and
one facet, a protrusive facet (f47), situated around a central fossa (S3),
wherein, of angles formed by the protrusive facet (f39) near the mesiobuccal cusp apex (C14) with the occlusal plane (P1), the angle in cross section along the sagittal plane (P2) is 23.5° to 32.0°, and the angle in cross section along the coronal plane (P3) is 7.0° to 15.0°,
wherein, of angles formed by the retrusive facet (f40) near the mesiobuccal cusp apex (C14) with the occlusal plane (P1), the angle in cross section along the sagittal plane (P2) is 7.5° to 12.0°, and the angle in cross section along the coronal plane (P3) is 14.0° to 16.0°,
wherein, of angles formed by the balancing facet (f41) near the mesiobuccal cusp apex (C14) with the occlusal plane (P1), the angle in cross section along the sagittal plane (P2) is 2.0° to 5.5°, and the angle in cross section along the coronal plane (P3) is 30.0° to 32.0°,
wherein, of angles formed by the protrusive facet (f42) near the distobuccal cusp apex (C15) with the occlusal plane (P1), the angle in cross section along the sagittal plane (P2) is 15.5° to 21.0°, and the angle in cross section along the coronal plane (P3) is 8.0° to 11.0°,
wherein, of angles formed by the retrusive facet (f43) near the distobuccal cusp apex (C15) with the occlusal plane (P1), the angle in cross section along the sagittal plane (P2) is 25.0° to 27.0°, and the angle in cross section along the coronal plane (P3) is 24.0° to 25.0°,
wherein, of angles formed by the balancing facet (f44) near the distobuccal cusp apex (C15) with the occlusal plane (P1), the angle in cross section along the sagittal plane (P2) is 12.0° to 20.0°, and the angle in cross section along the coronal plane (P3) is 30.0° to 37.0°, wherein, of angles formed by the protrusive facet (f45) near the distal cusp apex (C16) with the occlusal plane (P1), the angle in cross section along the sagittal plane (P2) is 7.5° to 13.0°, and the angle in cross section along the coronal plane (P3) is 10.0° to 13.0°, wherein, of angles formed by the balancing facet (f46) near the distal cusp apex (C16) with the occlusal plane (P1), the angle in cross section along the sagittal plane (P2) is 2.5° to 4.5°, and the angle in cross section along the coronal plane (P3) is 27.0° to 33.0° and wherein, of angles formed by the protrusive facet (f47) near the central fossa (S3) with the occlusal plane (P1), the angle in cross section along the sagittal plane (P2) is 10.5° to 18.5°, and the angle in cross section along the coronal plane (P3) is 1.0° to 8.0°;

wherein the facets make the following contacts in intercuspation, the protrusive facet (f13) of the artificial tooth for maxillary first molar (T6) contacts the protrusive facet (f42) of the artificial tooth for mandibular first molar (T13)

the retrusive facet (f14) of the artificial tooth for maxillary first molar (T6) contacts the retrusive facet (f40) of the artificial tooth for mandibular first molar (T13), the protrusive facet (f15) of the artificial tooth for maxillary first molar (T6) contacts the protrusive facet (f45) of the artificial tooth for mandibular first molar (T13)

the retrusive facet (f16) of the artificial tooth for maxillary first molar (T6) contacts the retrusive facet (f43) of the artificial tooth for mandibular first molar (T13), the balancing facet (f17) of the artificial tooth for maxillary first molar (T6) contacts the balancing facet (f44) of the artificial tooth for mandibular first molar (T13), and the protrusive facet (f18) of the artificial tooth for maxillary first molar (T6) contacts the protrusive facet (f47) of the artificial tooth for mandibular first molar (T13);

wherein the facets have the following gliding motility when functioning as a working side in lateral movements, the retrusive facet (f14) of the artificial tooth for maxillary first molar (T6) glides along the retrusive facet (f40) of the artificial tooth for mandibular first molar (T13), the retrusive facet (f16) of the artificial tooth for maxillary first molar (T6) glides along the retrusive facet (f43) of the artificial tooth for mandibular first molar (T13), and the protrusive facet (f18) of the artificial tooth for maxillary first molar (T6) glides along the protrusive facet (f47) of the artificial tooth for mandibular first molar (T13);

wherein the facets have the following gliding motility when functioning as a balancing side in lateral movements, the balancing facet (f17) of the artificial tooth for maxillary first molar (T6) glides along the balancing facet (f44) of the artificial tooth for mandibular first molar (T13); and wherein the facets have the following gliding motility in protrusive movements, the protrusive facet (f13) of the artificial tooth for maxillary first molar (T6) glides along the protrusive facet (f42) of the artificial tooth for mandibular first molar (T13), the protrusive facet (f15) of the artificial tootlifor maxillary first molar (T6) glides along the protrusive facet (f45) of the artificial tooth for mandibular first molar (T13), and the balancing facet (f18) of the artificial tooth for maxillary first molar (T6) glides along the protrusive facet (f47) of the artificial tooth for mandibular first molar (T13).

4. A set of artificial teeth comprising:

an artificial tooth for maxillary second molar (T7) having two facets, a protrusive facet (f21) and a retrusive facet (f22), situated around a mesiobuccal cusp apex (C9), one facet, a retrusive facet (f23), situated around a distobuccal cusp apex (C10), and two facets a protrusive facet (f25) and a balancing facet (f24), situated around a mesiolingual cusp apex (C11), wherein, of angles formed by the protrusive facet (f21) near the mesiobuccal cusp apex (C9) with an occlusal plane (P1), the angle in cross section along a sagittal plane (P2) is 22.5° to 25.5°, and the angle in cross section along a coronal plane (P3) is 1.0° to 2.5°, wherein, of angles formed by the retrusive facet (f22) near the mesiobuccal cusp apex (C9) with the occlusal plane (P1), the angle in cross section along the sagittal plane (P2) is 9.5° to 17.5°, and the angle in cross section along the coronal plane (P3) is 13.0° to 16.5°, wherein, of angles formed by the retrusive facet (f23) near the distobuccal cusp apex (C10) with the occlusal plane (P1), the angle in cross section along the sagittal plane (P2) is 6.5° to 12.0°, and the angle in cross section along the coronal plane (P3) is 4.5° to 7.0°, wherein, of angles formed by the balancing facet (f24) near the mesiolingual cusp apex (C11) with the occlusal plane (P1), the angle in cross section along the sagittal plane (P2) is 0.5° to 10.0°, and the angle in cross section along the coronal plane (P3) is 38.5° to 47.0°, and wherein, of angles formed by the protrusive facet (f25) near the mesiolingual cusp apex (C11) with the occlusal plane (P1), the angle in cross section along the sagittal plane (P2) is 20.5° to 22.5°, and the angle in cross section along the coronal plane (P3) is 1.5° to 6.0°; and an artificial tooth for mandibular second molar (T14) having three facets, a protrusive facet (f48), a retrusive facet (f49) and a balancing facet (f50), situated around a mesiobuccal cusp apex (C17), three facets, a protrusive facet (f51), a retrusive facet (f52) and a balancing facet (f53), situated around a distobuccal cusp apex (C18), and one facet, a protrusive facet (f54), situated around a central fossa (S4), wherein, of angles formed by the protrusive facet (f48) near the mesiobuccal cusp apex (C17) with the occlusal plane (P1), the angle in cross section along the sagittal plane (P2) is 26.0° to 30.0°, and the angle in cross section along the coronal plane (P3) is 10.0° to 13.0°, wherein, of angles formed by the retrusive facet (f49) near the mesiobuccal cusp apex (C17) with the occlusal plane (P1), the angle in cross section along the sagittal plane (P2) is 14.0° to 16.0°, and the angle in cross section along the coronal plane (P3) is 15.0° to 17.5°, wherein, of angles formed by the balancing facet (f50) near the mesiobuccal cusp apex (C17) with the occlusal plane (P1), the angle in cross section along the sagittal plane (P2) is 2.5° to 3.5°, and the angle in cross section along the coronal plane (P3) is 34.0° to 38.0°, wherein, of angles formed by the protrusive facet (f51) near the distobuccal cusp apex (C18) with the occlusal plane (P1), the angle in cross section along the sagittal plane (P2) is 17.0° to 21.0°, and the angle in cross section along the coronal plane (P3) is 4.5° to 6.5°, wherein, of angles formed by the retrusive facet (f52) near the distobuccal cusp apex (C18) with the occlusal plane (P1), the angle in cross section along the sagittal plane (P2) is 19.0° to 22.0°, and the angle in cross section along the coronal plane (P3) is 13.0° to 14.5°, wherein, of angles formed by the balancing facet (f53) near the distobuccal cusp apex (C18) with the occlusal plane (P1), the angle in cross section along the sagittal plane (P2) is 1.0° to 3.0°, and the angle in cross section along the coronal plane (P3) is 34.0° to 38.0°, and wherein, of angles formed by the protrusive facet (f54) near the central fossa (S4) with the occlusal plane (P1), the angle in cross section along the sagittal plane (P2) is 15.5° to 23.0°, and the angle in cross section along the coronal plane (P3) is 5.5° to 12.0°;

wherein the facets make the following contacts in intercuspation the protrusive facet (f21) of the artificial tooth for maxillary second molar (T7) contacts the protrusive facet (f51) of the artificial tooth for mandibular second molar (T14), the retrusive facet (f22) of the artificial tooth for maxillary second molar (T7) contacts the retrusive facet (f49) of the artificial tooth for mandibular second molar (T14), the retrusive facet (f23) of the artificial tooth for maxillary second molar (T7) contacts the retrusive facet (f52) of the artificial tooth for mandibular second molar (T14), the balancing facet (f24) of the artificial tooth for maxillary second molar (T7) contacts the balancing facet (f53) of the artificial tooth for mandibular second molar (T14), and the protrusive facet (f25) of the artificial tooth for maxillary second molar (T7) contacts the protrusive facet (f54) of the artificial tooth for mandibular second molar (T14);

wherein the facets have the following gliding motility when functioning as a working side in lateral movements, the retrusive facet (f22) of the artificial tooth for maxillary second molar (T7) glides along the retrusive facet (f49) of the artificial tooth for mandibular second molar (T14), the retrusive facet (f23) of the artificial tooth for maxillary second molar (T7) glides along the retrusive facet (f52) of the artificial tooth for mandibular second molar (T14), and the protrusive facet (f25) of the artificial tooth for maxillary second molar (T7) glides along the protrusive facet (f54) of the artificial tooth for mandibular second molar (T14);

wherein the facets have the following gliding motility when functioning as a balancing side in lateral movements, the balancing facet (f24) of the artificial tooth for maxillary second molar (T7) glides along the balancing facet (f53) of the artificial tooth for mandibular second molar (T14); and wherein the facets have the following gliding motility in protrusive movements, the protrusive facet (f21) of the artificial tooth for maxillary second molar (T7) glides along the protrusive facet (f51) of the artificial tooth for mandibular second molar (T14), and the protrusive facet (f25) of the artificial tooth for maxillary second molar (T7) glides along the protrusive facet (f54) of the artificial tooth for mandibular second molar (T14).

5. A set of artificial teeth comprising:

an artificial tooth for maxillary first premolar (T4) on a working side, and an artificial tooth for maxillary first premolar (T4) on a balancing side, each artificial tooth for maxillary first premolar (T4) having two facets, a protrusive facet (f7) and a retrusive facet (f8), situated around a buccal cusp apex (C1), and one facet, a balancing facet (f9), situated around a lingual cusp apex (C2), wherein, of angles formed by the protrusive facet (f7) near the buccal cusp apex (C1) with an occlusal plane (P1), the angle in cross section along a sagittal plane (P2) is 24.5° to 27.5°, and the angle in cross section along a coronal plane (P3) is 8.5° to 16.4°, wherein, of angles formed by the retrusive facet (f8) near the buccal cusp apex (C1) with the occlusal plane (P1), the angle in cross section along the sagittal plane (P2) is 18.5° to 27.0°, and the angle in cross section along the coronal plane is 10.0° to 18.0°, and wherein, of angles formed by the balancing facet (f9) near the lingual cusp apex (C2) with the occlusal plane(P1), the angle in cross section along the sagittal plane (P2) is 1.5° to 4.5°, and the angle in cross section along the coronal plane (P3) is 29.5° to 35.5°; and an artificial tooth for mandibular first premolar (T11) on the working side, and an artificial tooth for mandibular first premolar (T11) on the balancing side, each artificial tooth for mandibular first premolar (T11) having two facets, a protrusive facet (f31) and a retrusive facet (f32), situated around a buccal cusp apex (C12), one facet, a balancing facet (f33), situated along a distal marginal ridge, and one facet, a protrusive facet (f34), situated around a lingual cusp apex, wherein, of angles formed by the protrusive facet (f31) near the buccal cusp apex (C12) with the occlusal plane (P1), the angle in cross section along the sagittal plane (P2) is 38.0° to 41.0°, and the angle in cross section along the coronal plane (P3) is 5.0° to 8.5°, wherein, of angles formed by the retrusive facet (f32) near the buccal cusp apex (C12) with the occlusal plane (P1), the angle in cross section along the sagittal plane (P2) is 7.0° to 17.5°, and the angle in cross section along the coronal plane (P3) is 9.0° to 15.5°, wherein, of angles formed by the balancing facet (f33) near the distal marginal ridge with the occlusal plane (P1), the angle in cross section along the sagittal plane (P2) is 15.0° to 24.0°, and the angle in cross section along the coronal plane (P3) is 29.0° to 32.0°, and wherein, of angles formed by the protrusive facet (f34) near the lingual cusp apex with the occlusal plane (P1), the angle in cross section along the sagittal plane (P2) is 3.5° to 10.0°, and the angle in cross section along the coronal plane (P3) is 1.0° to 5.0°;

wherein the facets make the following contacts in intercuspation, the retrusive facets (f8) of the artificial teeth for maxillary first premolars (T4) contact the retrusive facets (f32) of the artificial teeth for mandibular first premolars (T11), and the balancing facets (f9) of the artificial teeth for maxillary first premolars (T4) contact the balancing facets (f33) of the artificial teeth for mandibular first premolars (T11);

wherein, the facets have the following gliding motility in lateral movements, on the working side, the retrusive facet (f8) of the artificial tooth for maxillary first premolar (T4) glides along the retrusive facet (f32) of the artificial tooth for mandibular first premolar (T11), and at the same time, on the balancing side, the balancing facet (f9) of the artificial tooth for maxillary first premolar (T4) glides along the balancing facet (f33) of the artificial tooth for mandibular first premolar (T11).

6. A set of artificial teeth comprishig:

an artificial tooth for maxillary second premolar (T5) on a working side, and an artificial tooth for maxillary second prerholar (T5) on a balancing side, each artificial tooth for maxillary second premolar (T5) having two facets, a protrusive facet (f10) and a retrusive facet (f11), situated around a buccal cusp apex (C3), and one facet, a balancing facet (f12), situated around a lingual cusp apex (C4), wherein, of angles formed by the protrusive facet (f10) near the buccal cusp apex (C3) with an occlusal plane (P1), the angle in cross section along a sagittal plane (P2) is 23.0° to 28.0°, and the angle in cross section along a coronal plane (P3) is 10.0° to 19.0°, wherein, of angles formed by the retrusive facet (f11) near the buccal cusp apex (C3) with the occlusal plane (P1), the angle in cross section along the sagittal plane (P2) is 16.5° to 19.0°, and the angle in cross section along the coronal plane (P3) is 13.0° to 17.5°, and wherein, of angles formed by the balancing facet (f12) near the lingual cusp apex (C4) with the occlusal plane (P1), the angle in cross section along the sagittal plane (P2) is 6.0° to 10.0°, and the angle in cross section along the coronal plane (P3) is 25.5° to 29.0°; and an artificial tooth for mandibular second premolar (T12) on the working side, and an artificial tooth for mandibular second premolar (T12) on the balancing side, each artificial tooth for mandibular second premolar (T12) having two facets, a protrusive facet (f35) and a retrusive facet (f36), situated around a buccal cusp apex (C13), one facet, a balancing facet (f37), situated along a distal marginal ridge, and one facet, a protrusive facet (f38), situated around a lingual cusp apex, wherein, of angles formed by the protrusive facet (f35) near the buccal cusp apex (C13) with the occlusal plane (P1), the angle in cross section along the sagittal plane (P2) is 27.5° to 30.0°, and the angle in cross section along the coronal plane (P3) is 16.0° to 19.0°, wherein, of angles formed by the retrusive facet (f36) near the buccal cusp apex (C13) with the occlusal plane (P1), the angle in cross section along the sagittal plane (P2) is 13.0° to 15.0°, and the angle in cross section along the coronal plane (P3) is 17.0° to 24.0°, wherein, of angles formed by the balancing facet (f37) near the distal marginal ridge with the occlusal plane (P1), the angle in cross section along the sagittal plane (P2) is 1.5° to 17.0°, and the angle in cross section along the coronal plane (P3) is 10.0° to 16.5°, and wherein, of angles formed by the protrusive facet (f38) near the lingual cusp apex with the occlusal plane (P1), the angle in cross section along the sagittal plane (P2) is 2.0° to 5.0°, and the angle in cross section along the coronal plane (P3) is 12.0° to 14.5°;

wherein the facets make the following contacts in intercuspation, the retrusive facets (f11) of the artificial teeth for maxillary second premolars (T5) contact the retrusive facets (f36) of the artificial teeth for mandibular second premolars (T12), and the balancing facets (f12) of the artificial teeth for maxillary second premolars (T5) contact the balancing facets (f37) of the artificial teeth for mandibular second premolars (T12);

wherein the facets have the following gliding motility in lateral movements, on the working side, the retrusive facet (f11) of the artificial tooth for maxillary second premolar (T5) glides along the retrusive facet (f36) of the artificial tooth for mandibular second premolar (T12), and at the same time, on the balancing side, the balancing facet (f12) of the artificial tooth for maxillary second premolar (T5) glides along the balancing facet (f37) of the artificial tooth for mandibular second premolar (T12).

7. A set of artificial teeth comprising:

an artificial tooth for maxillary first molar (T6) on a working side, and an artificial tooth for maxillary first molar (T6) on a balancing side, each artificial tooth for maxillary first molar (T6) having two facets, a protrusive facet (f13) and a retrusive facet (f14), situated around a mesiobuccal cusp apex (C5), two facets, a protrusive facet (f15) and a retrusive facet (f16), situated around a distobuccal cusp apex (C6), two facets, a protrusive facet (f18) and a balancing facet (f17), situated around a mesiolingual cusp apex (C7), and two facets, a retrusive facet (f19) and a balancing facet (f20), situated around a distolingual cusp apex (C8), wherein, of angles formed by the protrusive facet (f13) near the mesiobuccal cusp apex (C5) with an occlusal plane (P1), the angle in cross section along a sagittal plane (P2) is 18.5° to 21.0°, and the angle in cross section along a coronal plane (P3) is 5.0° to 11.0°, wherein, of angles formed by the retrusive facet (f14) near the mesiobuccal cusp apex (C5) with the occlusal plane (P1), the angle in cross section along the sagittal plane (P2) is 7.0° to 12.0°, and the angle in cross section along the coronal plane (P3) is 9.0° to 13.0°, wherein, of angles formed by the protrusive facet (f15) near the distobuccal cusp apex (C6) with the occlusal plane (P1), the angle in cross section along the sagittal plane (P2) is 15.5° to 19.5°, and the angle in cross section along the coronal plane (P3) is 8.0° to 9.0°, wherein, of angles formed by the retrusive facet (f16) near the distobuccal cusp apex (C6) with the occlusal plane (P1), the angle in cross section along the sagittal plane (P2) is 18.5° to 23.0°, and the angle in cross section along the coronal plane (P3) is 11.0° to 13.5°, wherein, of angles formed by the balancing facet (f17) near the mesiolingual cusp apex (C7) with the occlusal plane (P1), the angle in cross section along the sagittal plane (P2) is 14.5° to 16.5°, and the angle in cross section along the coronal plane (P3) is 40.0° to 42.0°, wherein, of angles formed by the protrusive facet (f18) near the mesiolingual cusp apex (C7) with the occlusal plane (P1), the angle in cross section along the sagittal plane (P2) is 18.5° to 19.5°, and the angle in cross section along the coronal plane (P3) is 4.5° to 6.5°, wherein, of angles formed by the retrusive facet (f19) near the distolingual cusp apex (C8) with the occlusal plane (P1), the angle in cross section along the sagittal plane (P2) is 6.5° to 7.5°, and the angle in cross section along the coronal plane (P3) is 15.5° to 18.0°, and wherein, of angles formed by the balancing facet (f20) near the distolingual cusp apex (C8) with the occlusal plane (P1), the angle in cross section along the sagittal plane (P2) is 3.0° to 12.0°, and the angle in cross section along the coronal plane (P3) is 32.0° to 38.5°; and an artificial tooth for mandibular first molar (T13) on the working side, and an artificial tooth for mandibular first molar (T13) on the balancing side, each artificial tooth for mandibular first molar (T13) having three facets, a protrusive facet (f39), a retrusive facet (f40) and a balancing facet (f41), situated around a mesiobuccal cusp apex (C14), three facets, a protrusive facet (f42), a retrusive facet (f43) and a balancing facet (f44), situated around a distobuccal cusp apex (C15), two facets, a protrusive facet (f45) and a balancing facet (f46), situated around a distal cusp apex (C16), and one facet, a protrusive facet (f47), situated around a central fossa (S3), wherein, of angles formed by the protrusive facet (f39) near the mesiobuccal cusp apex (C14) with the occlusal plane (P1), the angle in cross section along the sagittal plane (P2) is 23.5° to 32.0°, and the angle in cross section along the coronal plane (P3) is 7.0° to 15.0°, wherein, of angles formed by the retrusive facet (f40) near the mesiobuccal cusp apex (C14) with the occlusal plane (P1), the angle in cross section along the sagittal plane (P2) is 7.5° to 12.0°, and the angle in cross section along the coronal plane (P3) is 14.0° to 16.0°, wherein, of angles formed by the balancing facet (f41) near the mesiobuccal cusp apex (C14) with the occlusal plane (P1), the angle in cross section along the sagittal plane (P2) is 2.0° to 5.5°, and the angle in cross section along the coronal plane (P3) is 30.0° to 32.0°, wherein, of angles formed by the protrusive facet (f42) near the distobuccal cusp apex (C15) with the occlusal plane (P1), the angle in cross section along the sagittal plane (P2) is 15.5° to 21.0°, and the angle in cross section along the coronal plane (P3) is 8.0° to 11.0°, wherein, of angles formed by the retrusive facet (f43) near the distobuccal cusp apex (C15) with the occlusal plane (P1), the angle in cross section along the sagittal plane (P2) is 25.0° to 27.0°, and the angle in cross section along the coronal plane (P3) is 24.0° to 25.0°, wherein, of angles formed by the balancing facet (f44) near the distobuccal cusp apex (C15) with the occlusal plane (P1), the angle in cross section along the sagittal plane (P2) is 12.0° to 20.0°, and the angle in cross section along the coronal plane (P3) is 30.0° to 37.0°, wherein, of angles formed by the protrusive facet (f45) near the distal cusp apex (C16) with the occlusal plane (P1), the angle in cross section along the sagittal plane (P2) is 7.5° to 13.0°, and the angle in cross section along the coronal plane (P3) is 10.0° to 13.0°, wherein, of angles formed by the balancing facet (f46) near the distal cusp apex (C16) with the occlusal plane (P1), the angle in cross section along the sagittal plane (P2) is 2.5° to 4.5°, and the angle in cross section along the coronal plane (P3) is 27.0° to 33.0°, and wherein, of angles formed by the protrusive facet (f47) near the central fossa (S3) with the occlusal plane (P1), the angle in cross section along the sagittal plane (P2) is 10.5° to 18.5°, and the angle in cross section along the coronal plane (P3) is 1.0° to 8.0°;

wherein the facets make the following contacts in intercuspation, the protrusive facets (f13) of the artificial teeth for maxillary first molars (T6) contact the protrusive facets (f42) of the artificial teeth for mandibular first molars (T13), the retrusive facets (f14) of the artificial teeth for maxillary first molars (T6) contact the retrusive facets (f40) of the artificial teeth for mandibular first molars (T13), the protrusive facets (f15) of the artificial teeth for maxillary first molars (T6) contact the protrusive facets (f45) of the artificial teeth for mandibular first molars (T13), the retrusive facets (f16) of the artificial teeth for maxillary first molars (T6) contact the retrusive facets (f43) of the artificial teeth for mandibular first molars (T13), the balancing facets (f17) of the artificial teeth for maxillary first molars (T6) contact the balancing facets (f44) of the artificial teeth for mandibular first molars (T13), and the protrusive facets (f18) of the artificial teeth for maxillary first molars (T6) contact the protrusive facets (f47) of the artificial teeth for mandibular first molars (T13);

wherein the facets have the following gliding motility in lateral movements, on the working side, the retrusive facet (f14) of the artificial tooth for maxillary first molar (T6) glides along the retrusive facet (f40) of the artificial tooth for mandibular first molar (T13), the retrusive facet (f16) of the artificial tooth for maxillary first molar (T6) glides along the retrusive facet (f43) of the artificial tooth for mandibular first molar (T13), and the protrusive facet (f18) of the artificial tooth for maxillary first molar (T6) glides along the protrusive facet (f47) of the artificial tooth for mandibular first molar (T13), and at the same time, on the balancing side, the balancing facet (f17) of the artificial tooth for maxillary first molar (T6) glides along the balancing facet (f44) of the artificial tooth for mandibular first molar (T13); and wherein the facets have the following gliding motility in protrusive movements, the protrusive facets (f13) of the artificial teeth for maxillary first molars (T6) glide along the protrusive facets (f42) of the artificial teeth for mandibular first molars (T13), the protrusive facets (f15) of the artificial teeth for maxillary first molars (T6) glide along the protrusive facets (f45) of the artificial teeth for mandibular first molars (T13), and the balancing facets (f18) of the artificial teeth for maxillary first molars (T6) glide along the protrusive facets (f47) of the artificial teeth for mandibular first molars (T13).

8. A set of artificial teeth comprising:

an artificial tooth for maxillary second molar (T7) on a working side, and an artificial tooth for maxillary second molar (T7) on a balancing side, each artificial tooth for maxillary second molar (T7) having two facets, a protrusive facet (f21) and a retrusive facet (f22), situated around a mesiobuccal cusp apex (C9), one facet, a retrusive facet (f23), situated around a distobuccal cusp apex (C10), and two facets, a protrusive facet (f25) and a balancing facet (f24), situated around a mesiolingual cusp apex (C11), wherein, of angles formed by the protrusive facet (f21) near the mesiobuccal cusp apex (C9) with an occlusal plane (P1), the angle in cross section along a sagittal plane (P2) is 22.5° to 25.5°, and the angle in cross section along a coronal plane (P3) is 1.0° to 2.5°, wherein, of angles formed by the retrusive facet (f22) near the mesiobuccal cusp apex (C9) with the occlusal plane (P1), the angle in cross section along the sagittal plane (P2) is 9.5° to 17.5°, and the angle in cross section along the coronal plane (P3) is 13.0° to 16.5°, wherein, of angles formed by the retrusive facet (f23) near the distobuccal cusp apex (C10) with the occlusal plane (P1), the angle in cross section along the sagittal plane (P2) is 6.5° to 12.0°, and the angle in cross section along the coronal plane (P3) is 4.5° to 7.0°, wherein, of angles formed by the balancing facet (f24) near the mesiolingual cusp apex (C11) with the occlusal plane (P1), the angle in cross section along the sagittal plane (P2) is 0.5° to 10.0°, and the angle in cross section along the coronal plane (P3) is 38.5° to 47.0°, and wherein, of angles formed by the protrusive facet (f25) near the mesiolingual cusp apex (C11) with the occlusal plane (P1), the angle in cross section along the sagittal plane (P2) is 20.5° to 22.5°, and the angle in cross section along the coronal plane (P3) is 1.5° to 6.0°; and an artificial tooth for mandibular second molar (T14) on the working side, and an artificial tooth for mandibular second molar (T14) on the balancing side, each artificial tooth for mandibular second molar (T14) having three facets, a protrusive facet (f48), a retrusive facet (f49) and a balancing facet (f50), situated around a mesiobuccal cusp apex (C17), three facets, a protrusive facet (f51), a retrusive facet (f52) and a balancing facet (f53), situated around a distobuccal cusp apex (C18), and one facet, a protrusive facet (f54), situated around a central fossa (S4), wherein, of angles formed by the protrusive facet (f48) near the mesiobuccal cusp apex (C17) with the occlusal plane (P1), the angle in cross section along the sagittal plane. (P2) is 26.0° to 30.0°, and the angle in cross section along the coronal plane (P3) is 10.0° to 13.0°, wherein, of angles formed by the retrusive facet (f49) near the mesiobuccal cusp apex (C17) with the occlusal plane (P1), the angle in cross section along the sagittal plane (P2) is 14.0° to 16.0°, and the angle in cross section along the coronal plane (P3) is 15.0° to 17.5°, wherein, of angles formed by the balancing facet (f50) near the mesiobuccal cusp apex (C17) with the occlusal plane (P1), the angle in cross section along the sagittal plane (P2) is 2.5° to 3.5°, and the angle in cross section along the coronal plane (P3) is 34.0° to 38.0°, wherein, of angles formed by the protrusive facet (f51) near the distobuccal cusp apex (C18) with the occlusal plane (P1), the angle in cross section along the sagittal plane (P2) is 17.0° to 21.0°, and the angle in cross section along the coronal plane (P3) is 4.5° to 6.5°, wherein, of angles formed by the retrusive facet (f52) near the distobuccal cusp apex (C18) with the occlusal plane (P1), the angle in cross section along the sagittal plane (P2) is 19.0° to 22.0°, and the angle in cross section along the coronal plane (P3) is 13.0° to 14.5°, wherein, of angles formed by the balancing facet (f53) near the distobuccal cusp apex (C18) with the occlusal plane (P1), the angle in cross section along the sagittal plane (P2) is 1.0° to 3.0°, and the angle in cross section along the coronal plane (P3) is 34.0° to 38.0, and wherein, of angles formed by the protrusive facet (f54) near the central fossa (S4) with the occlusal plane (P1), the angle in cross section along the sagittal plane (P2) is 15.5° to 23.0°, and the angle in cross section along the coronal plane (P3) is 5.5° to 12.0°;

wherein the facets make the following contacts in intercuspation, the protrusive facets (f21) of the artificial teeth for maxillary second molars (T7) contact the protrusive facets (f51) of the artificial teeth for mandibular second molars (T14), the retrusive facets (f22) of the artificial teeth for maxillary second molars (T7) contact the retrusive facets (f49) of the artificial teeth for mandibular second molars (T14), the retrusive facets (f23) of the artificial teeth for maxillary second molars (T7) contact the retrusive facets (f52) of the artificial teeth for mandibular second molars (T14), the balancing facets (f24) of the artificial teeth for maxillary second molars (T7) contact the balancing facets (f53) of the artificial teeth for mandibular second molars (T14), and the protrusive facets (f25) of the artificial teeth for maxillary second molars (T7) contact the protrusive facets (f54) of the artificial teeth for mandibular second molars (T14);

wherein the facets have the following gliding motility in lateral movements, on the working side, the retrusive facet (f22) of the artificial tooth for maxillary second molar (T7) glides along the retrusive facet (f49) of the artificial tooth for mandibular second molar (T14), the retrusive facet (f23) of the artificial tooth for maxillary second molar (T7) glides along the retrusive facet (f52) of the artificial tooth for mandibular second molar (T14), and the protrusive facet (f25) of the artificial tooth for maxillary second molar (T7) glides along the protrusive facet (f54) of the artificial tooth for mandibular second molar (T14), and at the same time, on the balancing side, the balancing facet (f24) of the artificial tooth for maxillary second molar (T7) glides along the balancing facet (f53) of the artificial tooth for mandibular second molar (T14); and wherein the facets have the following gliding motility in protrusive movements, the protrusive facets (f21) of the artificial teeth for maxillary second molars (T7) glide along the protrusive facets (f51) of the artificial teeth for mandibular second molars (T14), and the protrusive facets (f25) of the artificial teeth for maxillary second molars (T7) glide along the protrusive facets (f54) of the artificial teeth for mandibular second molars (T14).

9. A set of artificial teeth comprising:

an artificial tooth for maxillary central incisor (T1) on a working side, and an artificial tooth for maxillary central incisor (T1) on a balancing side, each artificial tooth for maxillary central incisor (T1) having two facets, a protrusive facet (f1) and a retrusive facet (f2), situated on an incisal edge (i1), wherein, of angles formed by the protrusive facet (f1) with an occlusal plane (P1), the angle in cross section along a sagittal plane (P2) is 22.0° to 25.5°, and the angle in cross section along a coronal plane (P3) is 1.5° to 6.5°, and wherein, of angles formed by the retrusive facet (f2) with the occlusal, plane (P1), the angle in cross section along the sagittal plane (P2) is 20.5° to 23.0°, and the angle in cross section along the coronal plane (P3) is 1.5° to 6.5°;

an artificial tooth for maxillary lateral incisor (T2) on the working side, and an artificial tooth for maxillary incisor (T2) on the balancing side, each artificial tooth for maxillary incisor (T2) having two facets, a protrusive facet (f3) and a retrusive facet (f4), situated on an incisal edge (i2), wherein, of angles formed by the protrusive facet (f3) with the occlusal plane (P1), the angle in cross section along the sagittal plane (P2) is 23.0° to 28.0°, and the angle in cross section along the coronal plane (P3) is 15.0° to 17.0°, and wherein, of angles formed by the retrusive facet (f4) with the occlusal plane (P1), the angle in cross section along the sagittal plane (P2) is 16.0° to 22.0°, and the angle in cross section along the coronal plane (P3) is 9.5° to 10.5°;

an artificial tooth for maxillary canine (T3) on the working side, and an artificial tooth for maxillary canine (T3) on the balancing side, each artificial tooth for maxillary canine (T3) having two facets, a protrusive facet (f5) and a retrusive facet (f6), situated on an incisal edge (i3), wherein, of angles formed by the protrusive facet (f5) with the occlusal plane (P1), the angle in cross section along the sagittal plane (P2) is 25.0° to 31.0°, and the angle in cross section along the coronal plane (P3) is 1.5° to 5.0°, and wherein, of angles formed by the retrusive facet (f6) with the occlusal plane (P1), the angle in cross section along the sagittal plane (P2) is 8.5° to 22.5°, and the angle in cross section along the coronal plane (P3) is 18.0° to 25.0;

an artificial tooth for maxillary first premolar (T4) on the working side, and an artificial tooth for maxillary first premolar (T4) on the balancing side, each artificial tooth for maxillary first premolar (T4) having two facets, a protrusive facet (f7) and a retrusive facet (f8), situated around a buccal cusp apex (C1), and one facet, a balancing facet (f9), situated around a lingual cusp apex (C2), wherein, of angles formed by the protrusive facet (f7) near the buccal cusp apex (C1) with the occlusal plane (P1), the angle in cross section along the sagittal plane (P2) is 24.5° to 27.5°, and the angle in cross section along the coronal plane (P3) is 8.5° to 16.4°, wherein, of angles formed by the retrusive facet (f8) near the buccal cusp apex (C1) with the occlusal plane (P1), the angle in cross section along the sagittal plane (P2) is 18.5° to 27.0°, and the angle in cross section along the coronal plane is 10.0° to 18.0°, and wherein, of angles formed by the balancing facet (f9) near the lingual cusp apex (C2) with the occlusal plane(P1), the angle in cross section along the sagittal plane (P2) is 1.5° to 4.5°, and the angle in cross section along the coronal plane (P3) is 29.5° to 35.5°;

an artificial tooth for maxillary second premolar (T5) on a working side, and an artificial tooth for maxillary second premolar (T5) on a balancing side, each artificial tooth for maxillary second premolar (T5) having two facets, a protrusive facet (f10) and a retrusive facet (f11), situated around a buccal cusp apex (C3), and one facet, a balancing facet (f12), situated around a lingual cusp apex (C4), wherein, of angles formed by the protrusive facet (f10) near the buccal cusp apex (C3) with the occlusal plane (P1), the angle in cross section along the sagittal plane (P2) is 23.0° to 28.0°, and the angle in cross section along the coronal plane (P3) is 10.0° to 19.0°, wherein, of angles formed by the retrusive facet (f11) near the buccal cusp apex (C3) with the occlusal plane (P1), the angle in cross section along the sagittal plane (P2) is 16.5° to 19.0°, and the angle in cross section along the coronal plane (P3) is 13.0° to 17.5°, and wherein, of angles formed by the balancing facet (f12) near the lingual cusp apex (C4) with the occlusal plane (P1), the angle in cross section along the sagittal plane (P2) is 6.0° to 10.0°, and the angle in cross section along the coronal plane (P3) is 25.5° to 29.0°;

an artificial tooth for maxillary first molar (T6) on a working side, and an artificial tooth for maxillary first molar (T6) on a balancing side, each artificial tooth for maxillary first molar (T6) having two facets, a protrusive facet (f13) and a retrusive facet (f14), situated around a mesiobuccal cusp apex (C5), two facets, a protrusive facet (f15) and a retrusive facet (f16), situated around a distobuccal cusp apex (C6)

two facets, a protrusive facet (f18) and a balancing facet (f17), situated around a mesiolingual cusp apex (C7), and two facets, a retrusive facet (f19) and a balancing facet (f20), situated around a distolingual cusp apex (C8), wherein, of angles formed by the protrusive facet (f13) near the mesiobuccal cusp apex (C5) with the occlusal plane (P1), the angle in cross section along the sagittal plane (P2) is 18.5° to 21.0°, and the angle in cross section along the coronal plane (P3) is 5.0° to 11.0°, wherein, of angles formed by the retrusive facet (f14) near the mesiobuccal cusp apex (C5) with the occlusal plane (P1), the angle in cross section along the sagittal plane (P2) is 7.0° to 12.0°, and the angle in cross section along the coronal plane (P3) is 9.0° to 13.0°, wherein, of angles formed by the protrusive facet (f15) near the distobuccal cusp apex (C6) with the occlusal plane (P1), the angle in cross section along the sagittal plane (P2) is 15.5° to 19.5°, and the angle in cross section along the coronal plane (P3) is 8.0° to 9.0°, wherein, of angles formed by the retrusive facet (f16) near the distobuccal cusp apex (C6) with the occlusal plane (P1), the angle in cross section along the sagittal plane (P2) is 18.5° to 23.0°, and the angle in cross section along the coronal plane (P3) is 11.0° to 13.5°, wherein, of angles formed by the balancing facet (f17) near the mesiolingual cusp apex (C7) with the occlusal plane (P1), the angle in cross section along the sagittal plane (P2) is 14.5° to 16.5°, and the angle in cross section along the coronal plane (P3) is 40.0° to 42.0°, wherein, of angles formed by the protrusive facet (f18) near the mesiolingual cusp apex (C7) with the occlusal plane (P1), the angle in cross section along the sagittal plane (P2) is 18.5° to 19.5°, and the angle in cross section along the coronal plane (P3) is 4.5° to 6.5°, wherein, of angles formed by the retrusive facet (f19) near the distolingual cusp apex (C8) with the occlusal plane (P1), the angle in cross section along the sagittal plane (P2) is 6.5° to 7.5°, and the angle in cross section along the coronal plane (P3) is 15.5° to 18.0°, and wherein, of angles formed by the balancing facet (f20) near the distolingual cusp apex (C8) with the occlusal plane (P1), the angle in cross section along the sagittal plane (P2) is 3.0° to 12.0°, and the angle in cross section along the coronal plane (P3) is 32.0° to 38.5°;

an artificial tooth for maxillary second molar (T7) on a working side, and an artificial tooth for maxillary second molar (T7) on a balancing side, each artificial tooth for maxillary second molar (T7) having two facets, a protrusive facet (f21) and a retrusive facet (f22), situated around a mesiobuccal cusp apex (C9), one facet, a retrusive facet (f23), situated around a distobuccal cusp apex (C10), and two facets, a protrusive facet (f25) and a balancing facet (f24), situated around a mesiolingual cusp apex (C11), wherein, of angles formed by the protrusive facet (f21) near the mesiobuccal cusp apex (C9) with the occlusal plane (P1), the angle in cross section along the sagittal plane (P2) is 22.5° to 25.5°, and the angle in cross section along the coronal plane (P3) is 1.0° to 2.5°, wherein, of angles formed by the retrusive facet (f22) near the mesiobuccal cusp apex (C9) with the occlusal plane (P1), the angle in cross section along the sagittal plane (P2) is 9.5° to 17.5°, and the angle in cross section along the coronal plane (P3) is 13.0° to 16.5°, wherein, of angles formed by the retrusive facet (f23) near the distobuccal cusp apex (C10) with the occlusal plane (P1), the angle in cross section along the sagittal plane (P2) is 6.5° to 12.0°, and the angle in cross section along the coronal plane (P3) is 4.5° to 7.0°, wherein, of angles formed by the balancing facet (f24) near the mesiolingual cusp apex (C11) with the occlusal plane (P1), the angle in cross section along the sagittal plane (P2) is 0.5° to 10.0°, and the angle in cross section along the coronal plane (P3) is 38.5° to 47.0°, and wherein, of angles formed by the protrusive facet (f25) near the mesiolingual cusp apex (C11) with the occlusal plane (P1), the angle in cross section along the sagittal plane (P2) is 20.5° to 22.5°, and the angle in cross section along the coronal plane (P3) is 1.5° to 6.0°;

an artificial tooth for mandibular central incisor (T8) on the working side, and an artificial tooth for mandibular central incisor (T8) on the balancing side, each artificial tooth for mandibular central incisor (T8) having one facet, a protrusive facet (f26), situated on an incisal edge (i4), wherein, of angles formed by the protrusive facet (f26) with the occlusal plane (P1), the angle in cross section along the sagittal plane (P2) is 27.0° to 35.0°, and the angle in cross section along the coronal plane (P3) is 3.5° to 12.5°;

an artificial tooth for mandibular lateral incisor (T9) for the working side, and an artificial tooth for mandibular lateral incisor (T9) for the balancing side, each artificial tooth for mandibular lateral incisor (T9) having two facets, a protrusive facet (f27) and a retrusive facet (f28), situated on an incisal edge (i5), wherein, of angles formed by the protrusive facet (f27) with the occlusal plane (P1), the angle in cross section along the sagittal plane (P2) is 31.0° to 35.0°, and the angle in cross section along the coronal plane (P3) is 0.0° to 1.5°, and wherein, of angles formed by the retrusive facet (f28) with the occlusal plane (P1), the angle in cross section along the sagittal plane (P2) is 22.0° to 35.0°, and the angle in cross section along the coronal plane (P3) is 17.5° to 26.5°;

an artificial tooth for mandibular canine (T10) for the working side, and an artificial tooth for mandibular canine (T10) for the balancing side, each artificial tooth for mandibular canine (T10) having two facets, a protrusive facet (f29) and a retrusive facet (f30), situated on an incisal edge (i6), wherein, of angles formed by the protrusive facet (f29) with the occlusal plane (P1), the angle in cross section along the sagittal plane (P2) is 23.0° to 28.0, and the angle in cross section along the coronal plane (P3) is 0.5° to 10.0°, and wherein, of angles formed by the retrusive facet (f30) with the occlusal plane (P1), the angle in cross section along the sagittal plane (P2) is 14.5° to 18.0°, and the angle in cross section along the coronal plane (P3) is 16.0° to 21.0°;

an artificial tooth for mandibular first premolar (T11) on the working side, and an artificial tooth for mandibular first premolar (T11) on the balancing side, each artificial tooth for mandibular first premolar (T11) having two facets, a protrusive facet (f31) and a retrusive facet (f32), situated around a buccal cusp apex (C12), one facet, a balancing facet (f33), situated along a distal marginal ridge, and one facet, a protrusive facet (f34), situated around a lingual cusp apex, wherein, of angles formed by the protrusive facet (f31) near the buccal cusp apex (C12) with the occlusal plane (P1), the angle in cross section along the sagittal plane (P2) is 38.0° to 41.0°, and the angle in cross section along the coronal plane (P3) is 5.0° to 8.5°, wherein, of angles formed by the retrusive facet (f32) near the buccal cusp apex (C12) with the occlusal plane (P1), the angle in cross section along the sagittal plane (P2) is 7.0° to 17.5°, and the angle in cross section along the coronal plane (P3) is 9.0° to 15.5°, wherein, of angles formed by the balancing facet (f33) near the distal marginal ridge with the occlusal plane (P1), the angle in cross section along the sagittal plane (P2) is 15.0° to 24.0°, and the angle in cross section along the coronal plane (P3) is 29.0° to 32.0°, and wherein, of angles formed by the protrusive facet (f34) near the lingual cusp apex with the occlusal plane (P1), the angle in cross section along the sagittal plane (P2) is 3.5° to 10.0°, and the angle in cross section along the coronal plane (P3) is 1.0° to 5.0°;

an artificial tooth for mandibular second premolar (T12) on the working side, and an artificial tooth for mandibular second premolar (T12) on the balancing side, each artificial tooth for mandibular second premolar (T12) having two facets, a protrusive facet (f35) and a retrusive facet (f36), situated around a buccal cusp apex (C13), one facet, a balancing facet (f37), situated along a distal marginal ridge, and one facet, a protrusive facet (f38), situated around a lingual cusp apex, wherein, of angles formed by the protrusive facet (f35) near the buccal cusp apex (C13) with the occlusal plane (P1), the angle in cross section along the sagittal plane (P2) is 27.5° to 30.0°, and the angle in cross section along the coronal plane (P3) is 16.0° to 19.0°, wherein, of angles formed by the retrusive facet (f36) near the buccal cusp apex (C13) with the occlusal plane (P1), the angle in cross section along the sagittal plane (P2) is 13.0° to 15.0°, and the angle in cross section along the coronal plane (P3) is 17.0° to 24.0°, wherein, of angles formed by the balancing facet (f37) near the distal marginal ridge with the occlusal plane (P1), the angle in cross section along the sagittal plane (P2) is 1.5° to 17.0°, and the angle in cross section along the coronal plane (P3) is 10.0° to 16.5°, and wherein, of angles formed by the protrusive facet (f38) near the lingual cusp apex with the occlusal plane (P1), the angle in cross section along the sagittal plane (P2) is 2.0° to 5.0°, and the angle in cross section along the coronal plane (P3) is 12.0° to 14.5°;

an artificial tooth for mandibular first molar (T13) on the working side, and an artificial tooth for mandibular first molar (T13) on the balancing side, each artificial tooth for mandibular first molar (T13) having three facets, a protrusive facet (f39), a retrusive facet (f40) and a balancing facet (f41), situated around a mesiobuccal cusp apex (C14), three facets, a protrusive facet (f42), a retrusive facet (f43) and a balancing facet (f44), situated around a distobuccal cusp apex (C15), two facets, a protrusive facet (f45) and a balancing facet (f46), situated around a distal cusp apex (C16), and one facet, a protrusive facet (f47), situated around a central fossa (S3), wherein, of angles formed by the protrusive facet (f39) near the mesiobuccal cusp apex (C14) with the occlusal plane (P1), the angle in cross section along the sagittal plane (P2) is 23.5° to 32.0°, and the angle in cross section along the coronal plane (P3) is 7.0° to 15.0°, wherein, of angles formed by the retrusive facet (f40) near the mesiobuccal cusp apex (C14) with the occlusal plane (P1), the angle in cross section along the sagittal plane (P2) is 7.5° to 12.0°, and the angle in cross section along the coronal plane (P3) is 14.0° to 16.0°, wherein, of angles formed by the balancing facet (f41) near the mesiobuccal cusp apex (C14) with the occlusal plane (P1), the angle in cross section along the sagittal plane (P2) is 2.0° to 5.5°, and the angle in cross section along the coronal plane (P3) is 30.0° to 32.0°, wherein, of angles formed by the protrusive facet (f42) near the distobuccal cusp apex (C15) with the occlusal plane (P1), the angle in cross section along the sagittal plane (P2) is 15.5° to 21.0°, and the angle in cross section along the coronal plane (P3) is 8.0° to 11.0°, wherein, of angles formed by the retrusive facet (f43) near the distobuccal cusp apex (C15) with the occlusal plane (P1), the angle in cross section along the sagittal plane (P2) is 25.0° to 27.0°, and the angle in cross section along the coronal plane (P3) is 24.0° to 25.0°, wherein, of angles formed by the balancing facet (f44) near the distobuccal cusp apex (C15) with the occlusal plane (P1), the angle in cross section along the sagittal plane (P2) is 12.0° to 20.0°, and the angle in cross section along the coronal plane (P3) is 30.0° to 37.0°, wherein, of angles formed by the protrusive facet (f45) near the distal cusp apex (C16) with the occlusal plane (P1), the angle in cross section along the sagittal plane (P2) is 7.5° to 13.0°, and the angle in cross section along the coronal plane (P3) is 10.0° to 13.0°, wherein, of angles formed by the balancing facet (f46) near the distal cusp apex (C16) with the occlusal plane (P1), the angle in cross section along the sagittal plane (P2) is 2.5° to 4.5°, and the angle in cross section along the coronal plane (P3) is 27.0° to 33.0°, and wherein, of angles formed by the protrusive facet (f47) near the central fossa (S3) with the occlusal plane (P1), the angle in cross section along the sagittal plane (P2) is 10.5° to 18.5°, and the angle in cross section along the coronal plane (P3) is 1.0° to 8.0°; and an artificial tooth for mandibular second molar (T14) on the working side, and an artificial tooth for mandibular second molar (T14) on the balancing side, each artificial tooth for mandibular second molar (T14) having three facets, a protrusive facet (f48), a retrusive facet (f49) and a balancing facet (f50), situated around a mesiobuccal cusp apex (C17), three facets, a protrusive facet (f51), a retrusive facet (f52) and a balancing facet (f53), situated around a distobuccal cusp apex (C18), and one facet, a protrusive facet (f54), situated around a central fossa (S4), wherein, of angles formed by the protrusive facet (f48) near the mesiobuccal cusp apex (C17) with the occlusal plane (P1), the angle in cross section along the sagittal plane (P2) is 26.0° to 30.0°, and the angle in cross section along the coronal plane (P3) is 10.0° to 13.0°, wherein, of angles formed by the retrusive facet (f49) near the mesiobuccal cusp apex (C17) with the occlusal plane (P1), the angle in cross section along the sagittal plane (P2) is 14.0° to 16.0°, and the angle in cross section along the coronal plane (P3) is 15.0° to 17.5°, wherein, of angles formed by the balancing facet (f50) near the mesiobuccal cusp apex (C17) with the occlusal plane (P1), the angle in cross section along the sagittal plane (P2) is 2.5° to 3.5°, and the angle in cross section along the coronal plane (P3) is 34.0° to 38.0°, wherein, of angles formed by the protrusive facet (f51) near the distobuccal cusp apex (C18) with the occlusal plane (P1), the angle in cross section along the sagittal plane (P2) is 17.0° to 21.0°, and the angle in cross section along the coronal plane (P3) is 4.5° to 6.5°, wherein, of angles formed by the retrusive facet (f52) near the distobuccal cusp apex (C18) with the occlusal plane (P1), the angle in cross section along the sagittal plane (P2) is 19.0° to 22.0°, and the angle in cross section along the coronal plane (P3) is 13.0° to 14.5°, wherein, of angles formed by the balancing facet (f53) near the distobuccal cusp apex (C18) with the occlusal plane (P1), the angle in cross section along the sagittal plane (P2) is 1.0° to 3.0°, and the angle in cross section along the coronal plane (P3) is 34.0° to 38.0°, and wherein, of angles formed by the protrusive facet (f54) near the central fossa (S4) with the occlusal plane (P1), the angle in cross section along the sagittal plane (P2) is 15.5° to 23.0°, and the angle in cross section along the coronal plane (P3) is 5.5° to 12.0°;

wherein the facets make the following contacts in intercuspation, the protrusive facets (f1) of the artificial teeth for maxillary central incisors (T1) contact the protrusive facets (f27) of the artificial teeth for mandibular lateral incisors (T9), the retrusive facets (f2) of the artificial teeth for maxillary central incisors (T1) contact the protrusive facets (f26) of the artificial teeth for mandibular central incisors (T8), the protrusive facets (f3) of the artificial teeth for maxillary lateral incisors (T2) contact the protrusive facets (f29) of the artificial teeth for mandibular canines (T10), the retrusive facets (f4) of the artificial teeth for maxillary lateral incisors (T2) contact the retrusive facets (f28) of the artificial teeth for mandibular lateral incisors (T9), the protrusive facets (f5) of the artificial teeth for maxillary canines (T3) contact the protrusive facets (f31) of the artificial teeth for mandibular first premolars (T11), the retrusive facets (f6) of the artificial teeth for maxillary canines (T3) contact the retrusive facets (f30) of the artificial teeth for mandibular canines (T10), the protrusive facets (f7) of the artificial teeth for maxillary first premolars (T4) contact the protrusive facets (f35) of the artificial teeth for mandibular second premolars (T12), the retrusive facets (f8) of the artificial teeth for maxillary first premolars (T4) contact a retrusive facets (f32) of the artificial teeth for mandibular first premolars (T11), the balancing facets (f9) of the artificial teeth for maxillary first premolars (T4) contact the balancing facets (f33) of the artificial teeth for mandibular first premolars (T11), the protrusive facets (f10) of the artificial teeth for maxillary second premolars (T5) contact the protrusive facets (f39) of the artificial teeth for mandibular first molars (T13), the retrusive facets (f11) of the artificial teeth for maxillary second premolars (T5) contact the retrusive facets (f36) of the artificial teeth for mandibular second premolars (T12), the balancing facets (f12) of the artificial teeth for maxillary second premolars (T5) contact the balancing facets (f37) of the artificial teeth for mandibular second premolars (T12), the protrusive facets (f13) of the artificial teeth for maxillary first molars (T6) contact the protrusive facets (f42) of the artificial teeth for mandibular first molars (T13), the retrusive facets (f14) of the artificial teeth for maxillary first molars (T6) contact the retrusive facets (f40) of the artificial teeth for mandibular first molars (T13), the protrusive facets (f15) of the artificial teeth for maxillary first molars (T6) contact the protrusive facets (f45) of the artificial teeth for mandibular first molars (T13), the retrusive facets (f16) of the artificial teeth for maxillary first molars (T6) contact the retrusive facets (f43) of the artificial teeth for mandibular first molars (T13), the balancing facets (f17) of the artificial teeth for maxillary first molars (T6) contact the balancing facets (f44) of the artificial teeth for mandibular first molars (T13), the protrusive facets (f18) of the artificial teeth for maxillary first molars (T6) contact the protrusive facets (f47) of the artificial teeth for mandibular first molars (T13), the protrusive facets (f21) of the artificial teeth for maxillary second molars (T7) contact the protrusive facets (f51) of the artificial teeth for mandibular second molars (T14), the retrusive facets (f22) of the artificial teeth for maxillary second molars (T7) contact the retrusive facets. (f49) of the artificial teeth for mandibular second molars (T14), the retrusive facets (f23) of the artificial teeth for maxillary second molars (T7) contact the retrusive facets (f52) of the artificial teeth for mandibular second molars (T14), the balancing facets (f24) of the artificial teeth for maxillary second molars (T7) contact the balancing facets (f53) of the artificial teeth for mandibular second molars (T14), and the protrusive facets (f25) of the artificial teeth for maxillary second molars (T7) contact the protrusive facets (f54) of the artificial teeth for mandibular second molars (T14);

wherein the facets have the following gliding motility in lateral movements, on the working side, the retrusive facet (f4) of the artificial tooth for maxillary lateral incisor (T2) glides along the retrusive facet (f28) of the artificial tooth for mandibular lateral incisor (T9), the retrusive facet (f6) of the artificial tooth for maxillary canine (T3) glides along the retrusive facet (f30) of the artificial tooth for mandibular canine (T10), the retrusive facet (f8) of the artificial tooth for maxillary first premolar (T4) glides along the retrusive facet (f32) of the artificial tooth for mandibular first premolar (T11), the retrusive facet (f11) of the artificial tooth for maxillary second premolar (T5) glides along the retrusive facet (f36) of the artificial tooth for mandibular second premolar (T12), the retrusive facet (f14) of the artificial tooth for maxillary first molar (T6) glides along the retrusive facet (f40) of the artificial tooth for mandibular first molar (T13), the retrusive facet (f16) of the artificial tooth for maxillary first molar (T6) glides along the retrusive facet (f43) of the artificial tooth for mandibular first molar (T13), the protrusive facet (f18) of the artificial tooth for maxillary first molar (T6) glides along the protrusive facet (f47) of the artificial tooth for mandibular first molar (T13), the retrusive facet (f22) of the artificial tooth for maxillary second molar (T7) glides along the retrusive facet (f49) of the artificial tooth for mandibular second molar (T14), the retrusive facet (f23) of the artificial tooth for maxillary second molar (T7) glides along the retrusive facet (f52) of the artificial tooth for mandibular second molar (T14), and the protrusive facet (f25) of the artificial tooth for maxillary second molar (T7) glides along the protrusive facet (f54) of the artificial tooth for mandibular second molar (T14), and at the same time, on the balancing side, the balancing facet (f9) of the artificial tooth for maxillary first premolar (T4) glides along the balancing facet (f33) of the artificial tooth for mandibular first premolar (T11), the balancing facet (f12) of the artificial tooth for maxillary second premolar (T5) glides along the balancing facet (f37) of the artificial tooth for mandibular second premolar (T12) and the balancing facet (f41) of the artificial tooth for mandibular first molar (T13), the balancing facet (f17) of the artificial tooth for maxillary first molar (T6) glides along the balancing facet (f44) of the artificial tooth for mandibular first molar (T13), the balancing facet (f20) of the artificial tooth for maxillary first molar (T6) glides along the balancing facet (f50) of the artificial tooth for mandibular second molar (T14), and the balancing facet (f24) of the artificial tooth for maxillary second molar (T7) glides along the balancing facet (f53) of the artificial tooth for mandibular second molar (T14); and wherein the facets have the following gliding motility in protrusive movements, the protrusive facets (f1) of the artificial teeth for maxillary central incisors (T1) glide along the protrusive facets (f27) of the artificial teeth for mandibular lateral incisors (T9), the retrusive facets (f2) of the artificial teeth for maxillary central incisors (T1) glide along the protrusive facets (f26) of the artificial teeth for mandibular central incisors (T8), the protrusive facets (f3) of the artificial teeth for maxillary lateral incisors (T2) glide along the protrusive facets (f29) of the artificial teeth for mandibular canines (T10), the protrusive facets (f5) of the artificial teeth for maxillary canines (T3) glide along the protrusive facets (f31) of the artificial teeth for mandibular first premolars (T11), the protrusive facets (f7) of the artificial teeth for maxillary first premolars (T4) glide along the protrusive facets (f35) of the artificial teeth for mandibular second premolars (T12), the protrusive facets (f10) of the artificial teeth for maxillary second premolars (T5) glide along the protrusive facets (f39) of the artificial teeth for mandibular first molars (T13), the protrusive facets (f13) of the artificial teeth for maxillary first molars (T6) glide along the protrusive facets (f42) of the artificial teeth for mandibular first molars (T13), the protrusive facets (f15) of the artificial teeth for maxillary first molars (T6) glide along the protrusive facets (f45) of the artificial teeth for mandibular first molars (T13) and the protrusive facets (f48) of the artificial teeth for mandibular second molars (T14), the balancing facets (f18) of the artificial teeth for maxillary first molars (T6) glide along the protrusive facets (f47) of the artificial teeth for mandibular first molars (T13), the protrusive facets (f21) of the artificial teeth for maxillary second molars (T7) glide along the protrusive facets (f51) of the artificial teeth for mandibular second molars (T14), and the protrusive facets (f25) of the artificial teeth for maxillary second molars (T7) glide along the protrusive facets (f54) of the artificial teeth for mandibular second molars (T14).

* * * * *

UNITED STATES PATENT AND TRADEMARK OFFICE
CERTIFICATE OF CORRECTION

| | | |
|---|---|---|
| PATENT NO. | : 8,128,404 B2 | Page 1 of 1 |
| APPLICATION NO. | : 12/680892 | |
| DATED | : March 6, 2012 | |
| INVENTOR(S) | : Hirokazu Satoh, Kunihiro Fujii and Noriyuki Negoro | |

It is certified that error appears in the above-identified patent and that said Letters Patent is hereby corrected as shown below:

Title Page at item (86): Please change §371 (c)(1), (2), (4) Date from "Mar. 20, 2010" to --Mar. 30, 2010--.

Signed and Sealed this
First Day of May, 2012

David J. Kappos
*Director of the United States Patent and Trademark Office*